US008032204B2

(12) United States Patent
Solar et al.

(10) Patent No.: US 8,032,204 B2
(45) Date of Patent: Oct. 4, 2011

(54) FIDUCIAL MARKER DEVICES, TOOLS, AND METHODS

(75) Inventors: Matthew S. Solar, Indialantic, FL (US); Thomas L. Bridges, Melbourne Beach, FL (US); David M. Lee, Melbourne Beach, FL (US); Mark S. Freas, Palm Bay, FL (US)

(73) Assignee: Medtronic, Inc., Minneapolis, MN (US)

( * ) Notice: Subject to any disclaimer, the term of this patent is extended or adjusted under 35 U.S.C. 154(b) by 151 days.

(21) Appl. No.: 12/619,512

(22) Filed: Nov. 16, 2009

(65) Prior Publication Data

US 2010/0063388 A1    Mar. 11, 2010

Related U.S. Application Data

(63) Continuation of application No. 10/688,801, filed on Oct. 17, 2003, now Pat. No. 7,643,867, which is a continuation-in-part of application No. 10/374,677, filed on Feb. 25, 2003, now Pat. No. 7,720,522.

(51) Int. Cl.
*A61B 5/05* (2006.01)
(52) U.S. Cl. ........ 600/426; 600/407; 600/410; 600/414; 600/424; 600/431; 378/20; 606/72; 606/130
(58) Field of Classification Search .................. 600/407, 600/410, 414, 424, 426, 431; 378/20; 606/72, 606/130
See application file for complete search history.

(56) References Cited

U.S. PATENT DOCUMENTS

| | | | |
|---|---|---|---|
| 2,650,588 | A | 9/1953 | Drew |
| 4,228,799 | A | 10/1980 | Anichkov et al. |
| 4,408,372 | A | 10/1983 | Kimura et al. |
| D274,117 | S | 6/1984 | Lapps |
| 4,583,538 | A | 4/1986 | Onik et al. |
| 4,629,451 | A | 12/1986 | Winters et al. |
| 4,630,375 | A | 12/1986 | Spolyar |
| 4,675,173 | A | 6/1987 | Widder |

(Continued)

FOREIGN PATENT DOCUMENTS

DE    9112356    2/1992

(Continued)

OTHER PUBLICATIONS

"Acustar", Z-KAT, Inc., http://www.z-kat.com/acustar.htm, (2002), 5 pages.

(Continued)

*Primary Examiner* — Brian Casler
*Assistant Examiner* — James Kish
(74) *Attorney, Agent, or Firm* — Scott A. Marks; Harness, Dickey & Pierce PLC

(57) ABSTRACT

This document discusses, among other things, fiducial marker devices, tools, and methods. One example illustrates a combined computed tomography (CT) imageable fiducial locator head, an integral bone screw, and an integral divot for receiving a positioning wand of an image-guided surgical (IGS) workstation. A further example includes a fluid/gel-absorbing coating or cover into which a magnetic resonance (MR) imageable fluid is introduced, thereby permitting both CT and MR imaging. Protective caps and collars may be used to protect the fiducial marker from mechanical impact and/or to guide the fiducial marker during affixation. A bull's-eye or other template is used to select a center of a substantially spherical fiducial marker head on an image, such as for use during patient registration.

24 Claims, 29 Drawing Sheets

U.S. PATENT DOCUMENTS

| | | | |
|---|---|---|---|
| 4,763,548 A | 8/1988 | Leibinger et al. | |
| D306,190 S | 2/1990 | Poulsen et al. | |
| 4,931,056 A | 6/1990 | Ghajar et al. | |
| 4,943,293 A | 7/1990 | Lee, Jr. | |
| 4,943,298 A | 7/1990 | Fujita et al. | |
| 4,945,914 A | 8/1990 | Allen | |
| 4,954,914 A | 9/1990 | Karita et al. | |
| 4,991,579 A * | 2/1991 | Allen | 600/426 |
| 5,016,639 A | 5/1991 | Allen | |
| 5,042,462 A | 8/1991 | Bremer | |
| 5,058,580 A | 10/1991 | Hazard | |
| 5,094,241 A | 3/1992 | Allen | |
| 5,098,435 A | 3/1992 | Stednitz et al. | |
| 5,119,817 A | 6/1992 | Allen | |
| 5,142,930 A | 9/1992 | Allen et al. | |
| 5,178,164 A | 1/1993 | Allen | |
| 5,186,174 A | 2/1993 | Schlondorff et al. | |
| 5,197,476 A | 3/1993 | Nowacki et al. | |
| 5,201,737 A | 4/1993 | Leibinger et al. | |
| 5,211,164 A | 5/1993 | Allen | |
| 5,222,499 A | 6/1993 | Allen et al. | |
| 5,230,338 A | 7/1993 | Allen et al. | |
| 5,263,980 A | 11/1993 | Leibinger et al. | |
| 5,299,253 A | 3/1994 | Wessels | |
| 5,300,075 A | 4/1994 | Gordon | |
| 5,300,076 A | 4/1994 | Leriche et al. | |
| 5,305,203 A | 4/1994 | Raab | |
| 5,368,030 A | 11/1994 | Zinreich et al. | |
| 5,383,454 A | 1/1995 | Bucholz | |
| 5,389,101 A | 2/1995 | Heilbrun et al. | |
| 5,394,457 A | 2/1995 | Leibinger et al. | |
| 5,394,875 A | 3/1995 | Lewis et al. | |
| 5,397,329 A | 3/1995 | Allen | |
| 5,417,692 A | 5/1995 | Goble et al. | |
| 5,468,242 A | 11/1995 | Reisberg et al. | |
| 5,469,847 A | 11/1995 | Zinreich et al. | |
| 5,494,034 A | 2/1996 | Schlondorff et al. | |
| 5,551,429 A | 9/1996 | Fitzpatrick et al. | |
| 5,558,091 A | 9/1996 | Acker et al. | |
| 5,566,081 A | 10/1996 | Yoshizawa et al. | |
| 5,575,794 A | 11/1996 | Walus et al. | |
| 5,590,215 A | 12/1996 | Allen | |
| 5,595,193 A | 1/1997 | Walus et al. | |
| 5,603,318 A | 2/1997 | Heilbrun et al. | |
| 5,636,255 A | 6/1997 | Ellis et al. | |
| 5,681,313 A | 10/1997 | Diez et al. | |
| 5,683,217 A | 11/1997 | Walther et al. | |
| 5,730,130 A | 3/1998 | Fitzpatrick et al. | |
| 5,743,899 A | 4/1998 | Zinreich | |
| 5,769,789 A | 6/1998 | Wang et al. | |
| 5,799,099 A | 8/1998 | Wang et al. | |
| 5,807,252 A | 9/1998 | Hassfeld et al. | |
| 5,807,396 A | 9/1998 | Raveh et al. | |
| 5,836,954 A | 11/1998 | Heilbrun et al. | |
| 5,851,183 A | 12/1998 | Bucholz | |
| 5,860,389 A | 1/1999 | Caldwell | |
| 5,871,445 A | 2/1999 | Bucholz | |
| 5,891,034 A | 4/1999 | Bucholz | |
| 5,916,164 A | 6/1999 | Fitzpatrick et al. | |
| 5,954,722 A | 9/1999 | Bono | |
| 5,957,934 A | 9/1999 | Rapoport et al. | |
| 5,968,047 A | 10/1999 | Reed | |
| 5,984,930 A | 11/1999 | Maciunas et al. | |
| 6,000,892 A | 12/1999 | Takasaki et al. | |
| 6,006,126 A | 12/1999 | Cosman | |
| 6,011,987 A | 1/2000 | Barnett | |
| 6,019,776 A | 2/2000 | Preissman et al. | |
| 6,052,477 A | 4/2000 | Wang et al. | |
| 6,071,291 A | 6/2000 | Forst et al. | |
| 6,073,044 A | 6/2000 | Fitzpatrick et al. | |
| 6,076,008 A | 6/2000 | Bucholz | |
| 6,082,366 A | 7/2000 | Andra et al. | |
| 6,096,048 A | 8/2000 | Howard, III et al. | |
| 6,102,914 A | 8/2000 | Bulstra et al. | |
| 6,146,390 A | 11/2000 | Heilbrun et al. | |
| 6,165,181 A | 12/2000 | Heilbrun et al. | |
| 6,167,295 A | 12/2000 | Cosman | |
| 6,168,780 B1 | 1/2001 | Andra et al. | |
| 6,181,960 B1 | 1/2001 | Jensen et al. | |
| 6,187,018 B1 | 2/2001 | Sanjay-Gopal et al. | |
| 6,206,890 B1 | 3/2001 | Truwit | |
| 6,226,548 B1 | 5/2001 | Foley et al. | |
| 6,236,875 B1 | 5/2001 | Bucholz et al. | |
| RE37,249 E | 6/2001 | Leibinger et al. | |
| 6,241,732 B1 | 6/2001 | Overaker et al. | |
| 6,261,300 B1 | 7/2001 | Carol et al. | |
| 6,273,896 B1 | 8/2001 | Franck et al. | |
| 6,282,437 B1 | 8/2001 | Franck et al. | |
| 6,298,262 B1 | 10/2001 | Franck et al. | |
| 6,304,768 B1 | 10/2001 | Blume et al. | |
| 6,306,126 B1 | 10/2001 | Moctezuma et al. | |
| 6,327,491 B1 | 12/2001 | Franklin et al. | |
| 6,333,971 B2 | 12/2001 | McCrory et al. | |
| 6,351,659 B1 * | 2/2002 | Vilsmeier | 600/407 |
| 6,351,662 B1 | 2/2002 | Franck et al. | |
| 6,381,485 B1 | 4/2002 | Hunter et al. | |
| 6,382,815 B1 | 5/2002 | Klearman et al. | |
| 6,402,757 B1 | 6/2002 | Moore, III et al. | |
| 6,405,072 B1 | 6/2002 | Cosman | |
| 6,419,680 B1 | 7/2002 | Cosman et al. | |
| 6,430,434 B1 | 8/2002 | Mittelstadt | |
| 6,454,769 B2 | 9/2002 | Wagner et al. | |
| 6,459,927 B1 | 10/2002 | Franklin et al. | |
| 6,464,706 B1 | 10/2002 | Winters | |
| 6,499,488 B1 | 12/2002 | Hunter et al. | |
| 6,546,277 B1 | 4/2003 | Franck et al. | |
| 6,565,573 B1 | 5/2003 | Ferrante et al. | |
| 6,694,168 B2 | 2/2004 | Traxel et al. | |
| 6,738,657 B1 | 5/2004 | Franklin et al. | |
| D493,198 S | 7/2004 | Starkel | |
| 6,865,907 B2 | 3/2005 | Andrews et al. | |
| 6,866,666 B1 | 3/2005 | Sinnott et al. | |
| 6,942,667 B1 | 9/2005 | Song | |
| 6,993,374 B2 | 1/2006 | Sasso | |
| RE39,133 E | 6/2006 | Clayton et al. | |
| D527,820 S | 9/2006 | Solar et al. | |
| D528,211 S | 9/2006 | Solar et al. | |
| 2001/0000186 A1 | 4/2001 | Bramlet et al. | |
| 2001/0004395 A1 | 6/2001 | McCrory et al. | |
| 2001/0010004 A1 | 7/2001 | Traxel et al. | |
| 2001/0027271 A1 | 10/2001 | Franck et al. | |
| 2001/0051807 A1 | 12/2001 | Grafton | |
| 2002/0028423 A1 | 3/2002 | Levisman | |
| 2002/0052610 A1 | 5/2002 | Skakoon et al. | |
| 2002/0087101 A1 | 7/2002 | Barrick et al. | |
| 2002/0156363 A1 | 10/2002 | Hunter et al. | |
| 2003/0040753 A1 | 2/2003 | Daum et al. | |
| 2003/0187351 A1 | 10/2003 | Franck et al. | |
| 2004/0019265 A1 | 1/2004 | Mazzocchi et al. | |
| 2004/0019365 A1 | 1/2004 | Ding et al. | |
| 2004/0030236 A1 | 2/2004 | Mazzocchi et al. | |
| 2004/0030237 A1 | 2/2004 | Lee et al. | |
| 2004/0078084 A1 | 4/2004 | Albertorio | |
| 2004/0122305 A1 | 6/2004 | Grimm et al. | |
| 2004/0167391 A1 | 8/2004 | Solar et al. | |
| 2004/0167393 A1 | 8/2004 | Solar et al. | |
| 2004/0254581 A1 | 12/2004 | Leclair | |
| 2005/0015032 A1 | 1/2005 | Stein | |
| 2005/0042574 A1 | 2/2005 | Lazarof | |
| 2005/0043735 A1 | 2/2005 | Ahmad | |
| 2005/0240188 A1 * | 10/2005 | Chow et al. | 606/72 |
| 2007/0225599 A1 | 9/2007 | Solar et al. | |

FOREIGN PATENT DOCUMENTS

| | | |
|---|---|---|
| EP | 0787467 | 8/1997 |
| EP | 0813846 | 12/1997 |
| EP | 0820736 | 1/1998 |
| EP | 1033113 | 9/2000 |
| EP | 1249207 | 10/2002 |
| RU | 2026648 | 1/1995 |
| WO | WO-9709929 | 3/1997 |
| WO | WO-9838908 A1 | 9/1998 |
| WO | WO-9911998 | 3/1999 |
| WO | WO-9916352 | 4/1999 |
| WO | WO-9940869 | 8/1999 |

| | | |
|---|---|---|
| WO | WO-0149197 | 7/2001 |
| WO | WO-0178015 | 10/2001 |
| WO | WO-2004075768 | 9/2004 |

OTHER PUBLICATIONS

"Bone Anchor", U.S. Appl. No. 10/405,881, filed Apr. 2, 2003.

"Multi-Modality Radiographic Markers", IZI Medical Products, http://www.izimet.com, (2002), pp. 1-12.

"Stryker Navigation System, The Smarter Vision-Image Guided Surgery", Stryker Leibinger, Inc., (2002) 8 pages.

Clarysse, P. et al. "A Computer-Assisted System for 3-D Frameless Localization in Stereotaxic MRI", IEEE Transactions on Medical Imaging, 10, (1991) 523-529.

Coste, E. et al., "Frameless Method of Sterotaxic Localization with DSA", Radiology, (1993), 829-834.

Leibinger et al., "Microsurgical Neurectomy Bayonet Scissors", The Leibinger Family of Neurosurgical Products, (1993) 1.

Leibinger et al., "The ZD Stereotactic System", Leibinger et al. v. McCrory et al., Interference No. 103,657 (1992), 19.

Leibinger, "Summary of Safety and Effectiveness", Marker System for Stereotaxic Navigation, (Mar. 1995), pp. 38-46.

Leibinger, et al., "The F.L. Fischer™ Stereotactic Products by Leibinger™", Leibinger et al. v. McCrory et al., Interference No. 103,657, (1993), 1.

Motti, E. D. et al., "Head-holder Interfacing Computed Tomography with Talairach Stereotactic Frame", Journal of Neurosurgical Sciences, 27(3), (1983), 219-223.

Office Action in U.S. Appl. No. 10/374,677 by James Kish, mailed Sep. 5, 2007.

Rousseau et al., "Validation of a New Method for Stereotactic Localization using MR Imaging", Journal of Computer Assisted Tomography, (1991) 291-296.

Rousseau, J. et al., "A frameless method for 3D MRI and CTstereotaxic localisation", European Radiology, (1992), pp. 1286-1292.

Solar, M. S. et al "Fiducial Marker", U.S. Appl. No. 29/199,266, filed Feb. 12, 2004, 17 pgs.

Waltregny et al., "Application of the Talairach stereotaxic system for the purpose of estalishing a common reference plane for brain imaging techniques (CAT scan, NMRI, PET scan)", Revue d'Electroencephalographic et de Neuro-physiologie Clinique, 16(3), (1986), 269-271.

* cited by examiner

FIDUCIAL MARKER DEVICES, TOOLS, AND METHODS

CROSS-REFERENCE TO RELATED APPLICATIONS

The present patent application is a continuation of U.S. patent application Ser. No. 10/688,801, filed on Oct. 17, 2003, which is a continuation-in-part (CIP) of related Solar et al. U.S. patent application Ser. No. 10/374,677, entitled "FIDUCIAL MARKER DEVICES, TOOLS, AND METHODS," filed on Feb. 25, 2003, and all of which are incorporated by reference herein in their entirety, including their disclosure of fiducial marker devices, tools, and methods.

The present patent application is also related to Mazzocchi et al. U.S. patent application Ser. No. 10/206,884, entitled "FIDUCIAL MARKER DEVICES, TOOLS, AND METHODS," filed on Jul. 24, 2002, and which is incorporated by reference herein in its entirety, including its disclosure of fiducial marker devices, tools, and methods.

The present patent application is also related to Mazzocchi et al. U.S. patent application Ser. No. 10/454,145, entitled "FIDUCIAL MARKER DEVICES, TOOLS, AND METHODS," filed on Jun. 4, 2003, and which is incorporated by reference herein in its entirety, including its disclosure of fiducial marker devices, tools, and methods.

FIELD

This document relates generally to imaging and/or locating a subject, such as for performing surgical intervention, and more specifically, but not by way of limitation, to fiducial marker devices and associated tools and methods.

BACKGROUND

Fiducial markers that can be located and recognized by an imaging system or other system are useful in neurosurgery and other applications. Examples of imaging system modalities include, among other things, magnetic resonance imaging (MRI), computed tomography (CT), positron emission tomography (PET), and single photon emission computed tomography (SPECT).

For example, in one technique, multiple fiducial markers are screwed into the patient's skull to define landmarks recognizable by an imaging system. The imaging system is used to obtain one or more preoperative images of the patient's brain. Recognizable images of the fiducial markers appear on such preoperative images. Such a bone-anchored fiducial marker typically includes an externally threaded bone-screw portion, which is driven into the skull. A threaded shaft rises up and out of the skull from the bone-screw. The threaded shaft typically receives a screwed-on imageable sphere that is visible on an MRI or CT image. The multiple fiducial markers on the patient's skull define landmarks on preoperative images that are useful to the physician for planning entry coordinates on the patient's skull and for planning a trajectory to a target location in the brain. An image-guided surgical workstation uses these preoperative images and the planning data to guide the neurosurgeon while actually performing the subsequent surgical procedure.

After the preoperative planning phase, the patient is brought into the operating room so that the planned surgical procedure can be performed. On the operating table, the patient's skull is clamped in a head-frame or otherwise immobilized. In order to use the preoperative images provided by the image-guided workstation to guide the surgeon during the surgical procedure, the patient's skull must first be "registered" to the preoperative images. The registration creates an association between (1) the actual physical location of the fiducial markers on the patient's skull in the operating room and (2) the locations of the images of the fiducial markers visible on the preoperatively-obtained images. This allows mapping between the actual space in which the patient is located to the space defined by the preoperative images.

According to one registration technique, a "wand" is used to perform this patient registration. The wand typically includes multiple light-emitting diode (LED) locators or reflective locators, which are visible to an infrared camera or other detector of an optical positioning system in the operating room. The camera and optical positioning system are operatively connected to the image-guided workstation. The locators define the position of the wand in the operating room, including the position of a sharp tip portion of the wand, which is in a known physical relationship to the locators. To register the patient, the imageable spheres are unscrewed from the fiducial marker shafts, and replaced by respective "divots" that are sized and shaped to receive the wand tip. These divots are screwed or otherwise engaged onto the respective fiducial marker shafts, such that when the wand tip is received into the maximum depression point of the divot, the wand tip then corresponds to the same location as the center of the imageable sphere when the imageable sphere was screwed onto the fiducial marker shaft. A reference divot is typically also present in the operating room at a known location, such as attached to the operating table or the patient's skull-immobilizing head-frame. During the patient registration process, the surgeon touches the wand tip to the reference divot (to provide an absolute positional reference to the image-guided workstation), and then to each fiducial marker divot. This permits the image-guided workstation to correlate the actual physical location of the patient's skull to the preoperative images. The physician can then use the wand, in conjunction with the preoperative images provided by the image-guided workstation, to locate an appropriate entry point and trajectory to the target in the brain.

The present inventors have recognized a streamlined registration process to reduce its time and cost. The streamlined process can reduce possible patient discomfort caused by the presence of the fiducial markers, reducing the number of members to be screwed into the patient resulting from using multiple fiducial markers screwed into different locations of the patient's skull. Reducing the number of members and thus reducing the difficulty of unscrewing the imaging spheres and replacing them with the registration divots. The streamlined process can also work with a limited field of view of the camera used in the operating room. Further, the streamline process is usable as a multi-modal fiducial marker that can be recognized by more than one imaging modality or positioning system.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1A is a schematic diagram illustrating generally one example of an imageable fiducial marker that includes a built-in conical divot or other male or female receptacle, or the like.

FIG. 2A is a schematic diagram illustrating generally an alternative example of a fiducial marker that includes a cylindrical imaging fiducial locator and a conical or other divot or other receptacle for receiving a positioning wand tip or the like.

FIG. 6A is a schematic diagram illustrating generally a divot assembly that includes a swiveling tilted head carrying a conical or other divot or the like.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

In this document, the term "assembly" is not intended to be limited to a structure that is assembled from multiple components, but also includes unitary or integrally-formed structures or the like.

Example 1

Figure 1A:
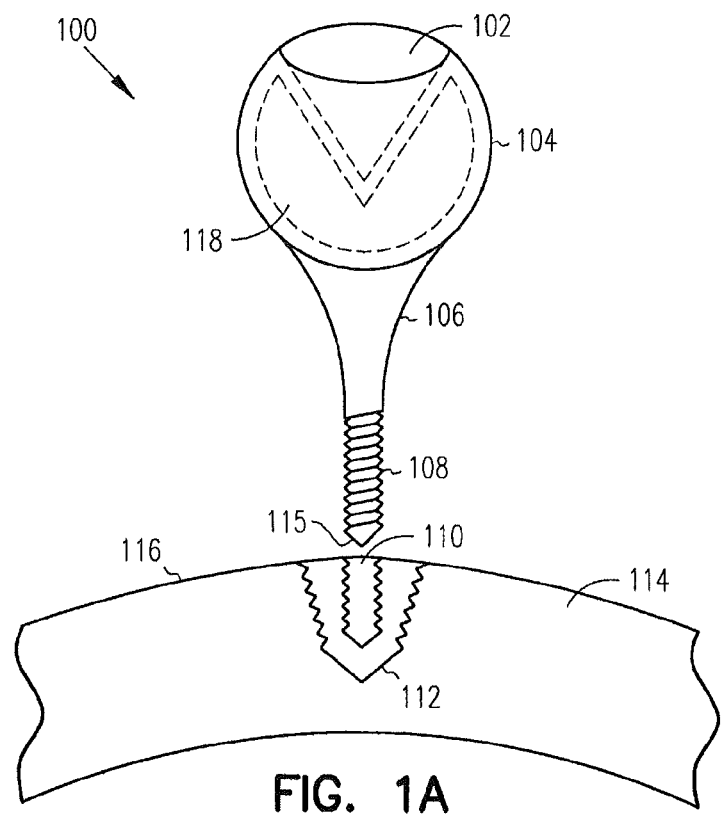

FIG. 1A is a schematic diagram illustrating generally, by way of example, but not by way of limitation, one example of an imageable fiducial marker 100 that includes a built-in divot 102. In this example, the divot 102 includes a female receptacle, such as the illustrated conical depression. However, as used herein, a divot also refers to any other male or female receptacle, or the like. The divot 102 is capable of receiving a correspondingly sized and shaped mating tip of a positioning wand or like instrument. Such a wand or instrument is useful for registering the actual physical location of the patient's skull to preoperative or other images of the subject's brain. Such images are typically stored in a memory of an image-guided surgical (IGS) computer workstation.

In the example illustrated in FIG. 1A, the fiducial marker 100 includes an imageable substantially spherical fiducial locator 104. The fiducial 104 is locatable using one or more imaging system modalities. In this example, a shaft 106 extends orthogonally outward from a circumferential portion of the spherical fiducial 104. The shaft 106 includes an externally threaded portion 108. The externally threaded portion 108 is sized and shaped for being received within a correspondingly sized and shaped mating internally threaded receptacle 110 of an externally-threaded self-tapping base 112. In this example, the base 112 is capable of being mounted in a skull 114, such as either flush to (or even recessed from) an outer surface 116 of the skull 114. One example of a suitable base 112 is described in commonly-assigned Mazzocchi et al. U.S. patent application Ser. No. 10/206,884 entitled FIDUCIAL MARKER DEVICES, TOOLS, AND METHODS, which was filed on Jul. 24, 2002, and which is incorporated herein by reference in its entirety, including its disclosure relating to a flush or recessed mounted base and other fiducial marker devices, tools and methods. However, in alternative examples, the base 112 need not be configured for mounting flush to or recessed from the outer surface 116 of the skull 114. In this example, the shaft 106 includes a pointed tip 115. This permits the shaft 106 to more easily penetrate a sterile drape that, in certain circumstances, may be placed over the patient's skull 114. Moreover, in this example, the receptacle 110 of the base 112 is shaped to accommodate the pointed tip 115. However, in an alternative example, the tip 115 need not be pointed.

In one example, the imaging spherical fiducial locator 104 houses a generally spherical (e.g., except for the conic cutaway of the divot 102) sealed interior cavity 118. In one example, the cavity 118 is filled with an imageable fluid that is visible on one or more imaging modalities (e.g., MR, CT, etc.). In this example, the apex of the conic divot 102 is located at a spherical center of mass of the imaging spherical fiducial locator 104 (i.e., the apex is located where the center of mass would be if the imaging fiducial locator 104 were perfectly spherical, without any cutout divot). This allows the tip of a positioning wand (recognizable by a camera in an optical position locating system that is coupled to the image-guided surgical workstation) to be inserted into the divot 102. This results in the wand tip being located at the spherical center of mass of the imaging spherical fiducial locator 104. This is useful for assisting in registering the physical location of the patient to the preoperative images stored in the image-guided surgical workstation.

Unlike fiducial marker assemblies that require the user to attach an imaging fiducial while obtaining the preoperative images of the patient's brain, and to then replace that imaging fiducial with a separate divot during patient registration in the operating room, the fiducial marker 100 illustrated in FIG. 1A does not require any such exchange of the imaging fiducial for a separate divot. Instead, the divot is integrated into the imaging fiducial itself, as illustrated in FIG. 1A. This reduces the complexity of the image-guided surgical procedure and, therefore, reduces its cost. It also reduces the complexity of manufacturing, which, in turn, reduces manufacturing costs.

In one example (but not by way of limitation), the base 112 is constructed of stainless steel. The shaft 106 and the imaging spherical fiducial locator 104 are constructed of molded plastic polymer. In this example, the imaging spherical fiducial locator 104 includes an open cavity 118 for receiving the imaging fluid, and for then receiving an insertable plastic conical divot 102 that adhesively or otherwise seals the cavity 118 to retain the imaging fluid therein. The imaging fluid in the cavity 118 is visible and provides good contrast on images produced by at least one imaging modality. In one example, the imaging fluid is multimodal (i.e., locatable by more than one imaging modality), such as by using a mixture of different imaging fluids that are locatable on different imaging modalities. In an alternative example, the plastic forming the imaging spherical fiducial locator 104 includes a substance that is viewable on a first imaging modality, while the imaging fluid within the cavity 118 is viewable on a different second imaging modality.

In one such illustrative example, the plastic imaging fiducial locator 104 is doped with a substance having a high atomic number (Z), such as barium, titanium, iodine, silver, gold, platinum, iodine, stainless steel, titanium dioxide, etc. that provide good contrast on a CT or other radiographic imaging system. In this illustrative example, the fluid within the cavity 118 includes gadopentatate dimeglumine, gadoteridol, ferric chloride, copper sulfate, or any other suitable MRI contrast agent, such as described in chapter 14 of Magnetic Resonance Imaging, $2^{nd}$ ed., edited by Stark and Bradley, 1992, which is incorporated herein by reference.

In an alternative multimodal example, the cavity 118 is omitted. Instead, the spherical fiducial locator 104 is constructed of a substantially solid plastic or other material that is hygroscopic, that is, capable of receiving and retaining a fluid, such as an imaging fluid that is viewable on an imaging system (e.g., an MRI imaging system or the like). In a further example, the plastic forming the spherical fiducial locator 104 is doped or otherwise includes a substance that is viewable on a different imaging system, such as, for example, a CT or other radiographic imaging system. Illustrative examples of solid plastics that can be made hygroscopic include, among other things, nylon and polyurethane. Using a hygroscopic material avoids the complexity and cost associated with manufacturing a sealed cavity 118 for retaining an imaging fluid. Moreover, by adapting the solid hygroscopic plastic for imaging using a first modality, and by using the imaging fluid for imaging using a second modality, each of the solid and the fluid can be separately tailored toward providing better contrast for its particular imaging modality.

In another alternative example in which the cavity 118 is omitted, the fiducial locator 104 includes a rigid solid (e.g., substantially spherical, but for the conic divot) interior. This solid material is doped with a substance that provides good contrast using a first imaging modality (e.g., CT). A hygroscopic outer coating is formed thereupon. The coating permits soaking up a fluid that provides a good contrast using a second imaging modality (e.g., MRI).

In a further example of the fiducial marker 100 illustrated in FIG. 1A, the outer surface of the imaging spherical fiducial locator 104 is reflective of light or other electromagnetic energy. Consequently, it is also locatable by the operating room camera in an optical positioning system that is coupled to the image-guided workstation (e.g., during patient registration). In one such example, the outer surface of the imaging spherical fiducial locator 104 includes light-reflective microspheres (e.g., embedded in an adhesive covering the imaging spherical fiducial 104). In another such example, the outer surface of the imaging spherical fiducial 104 is covered with an adhesive-backed light-reflective tape, such as SCOTCHLITE® 9810 Reflective Material Multipurpose Tape sold by Minnesota Mining and Manufacturing Co. ("3M®"), of Saint Paul, Minn.

Figure 2A:
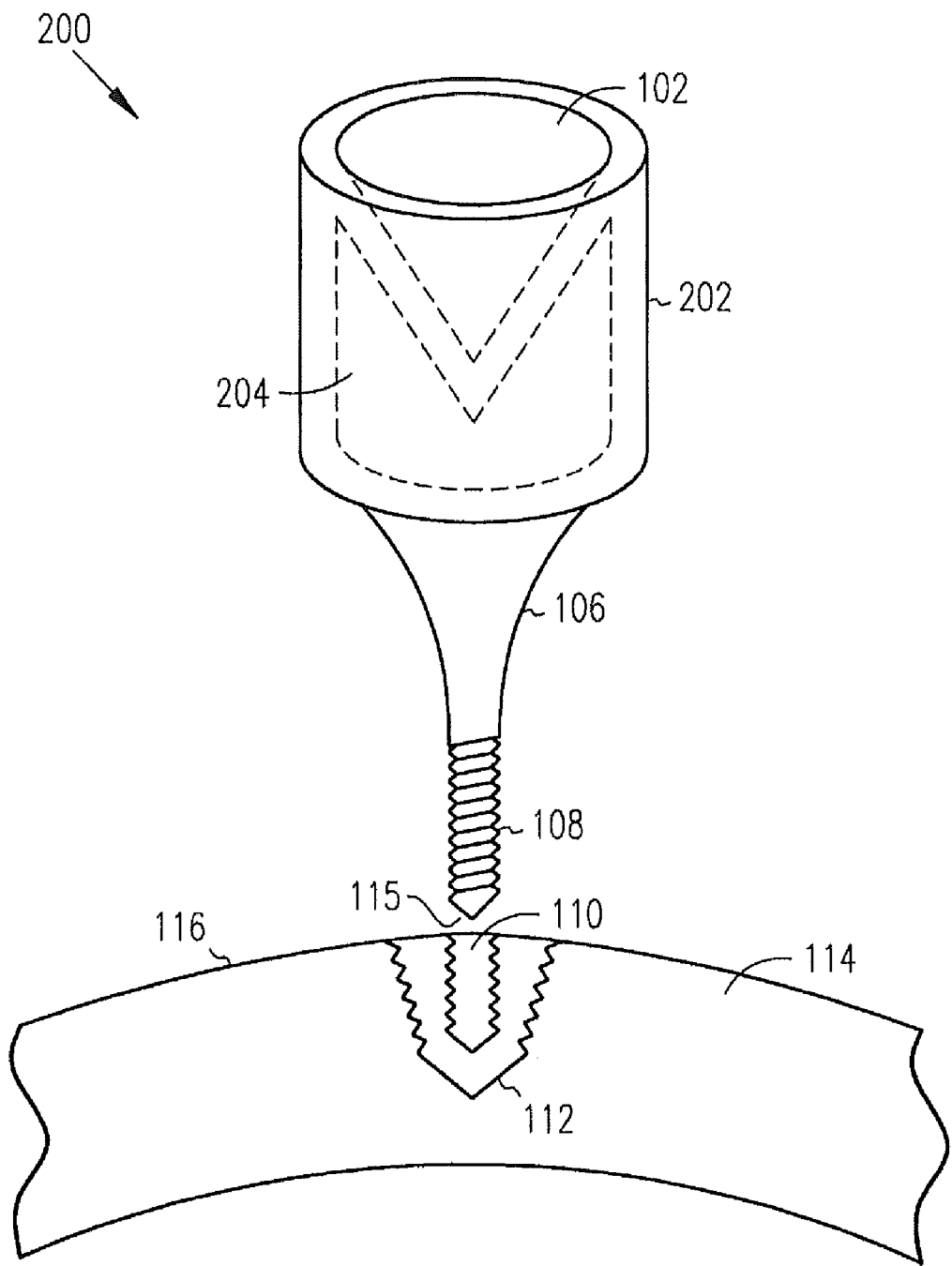

FIG. 2A is a schematic diagram illustrating generally, by way of example, but not by way of limitation, an alternative example of a fiducial marker 200 that includes a generally cylindrical imaging fiducial locator 202 and a conical or other divot 102. In one example, the generally cylindrical imaging fiducial locator 202 includes a sealed cavity 204 for receiving and retaining an imageable fluid, as discussed above. In another example, the sealed cavity 204 is omitted, as discussed above. In one such example, the generally cylindrical imaging fiducial locator 202 is instead constructed of a substantially solid hygroscopic plastic that carries an imageable fluid (as discussed above), such as for providing multimodal contrast across different imaging modalities. In a further example, the generally cylindrical outer surface of the imaging fiducial locator 202 is reflective, as discussed above, such that the imaging fiducial locator 202 is also visible to a camera of an optical position locating system that is coupled to an image-guided surgical workstation (e.g., during patient registration and/or a subsequent image-guided surgical procedure). In one such example, the imaging fiducial locator 202 is covered with adhesive-backed reflective tape taken from a rectangular strip of such tape that is wound into a roll. In this example, the generally cylindrical shape of the outer surface of the imaging fiducial locator 202 is much easier to wrap using a wound rectangular strip of the adhesive reflective tape than a spherical surface, such as is illustrated in FIG. 1A, and therefore costs less to manufacture. In this document, the term "generally cylindrical" is not limited to a perfectly cylindrical surface, but instead is understood to include any faceted or other column or like structure (e.g., an octogonal cylinder a hexagonal cylinder, etc.) that includes a lateral peripheral surface that easily accommodates receiving a wound rectangular or similar strip of tape (as opposed to a spherical, elliptical, or conical surface, to which is more difficult to evenly apply a wound rectangular strip of tape taken from a roll). Examples of such generally "cylindrical" columnar structures having faceted lateral peripheral surfaces are illustrated in FIG. 3C.

Figure 1B:
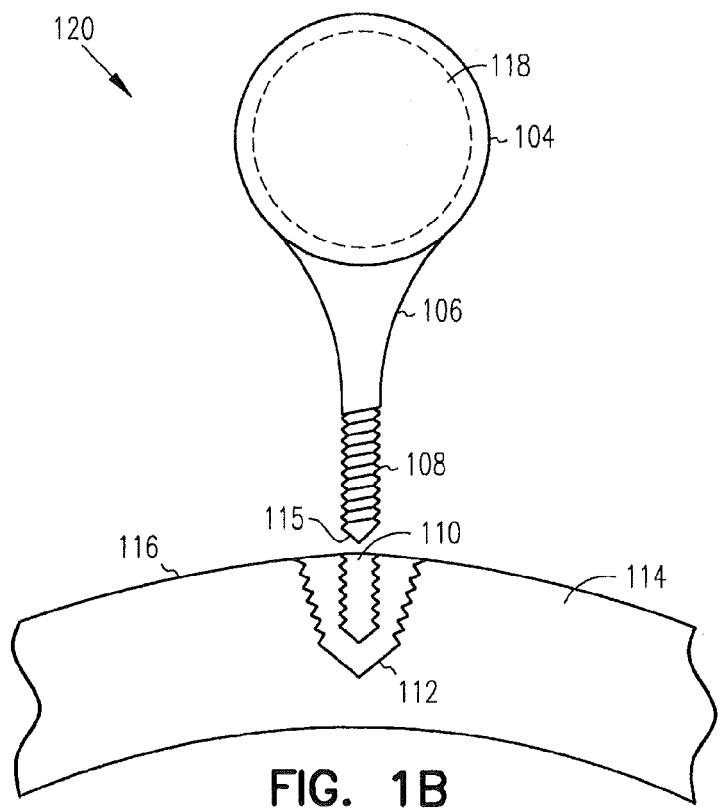
FIG. 1B is a schematic diagram illustrating generally one example of an imageable fiducial marker that omits the divot illustrated in FIG. 1A, but which is both locatable by a remote positioning system and imageable by one or more imaging modalities.
Figure 2B:
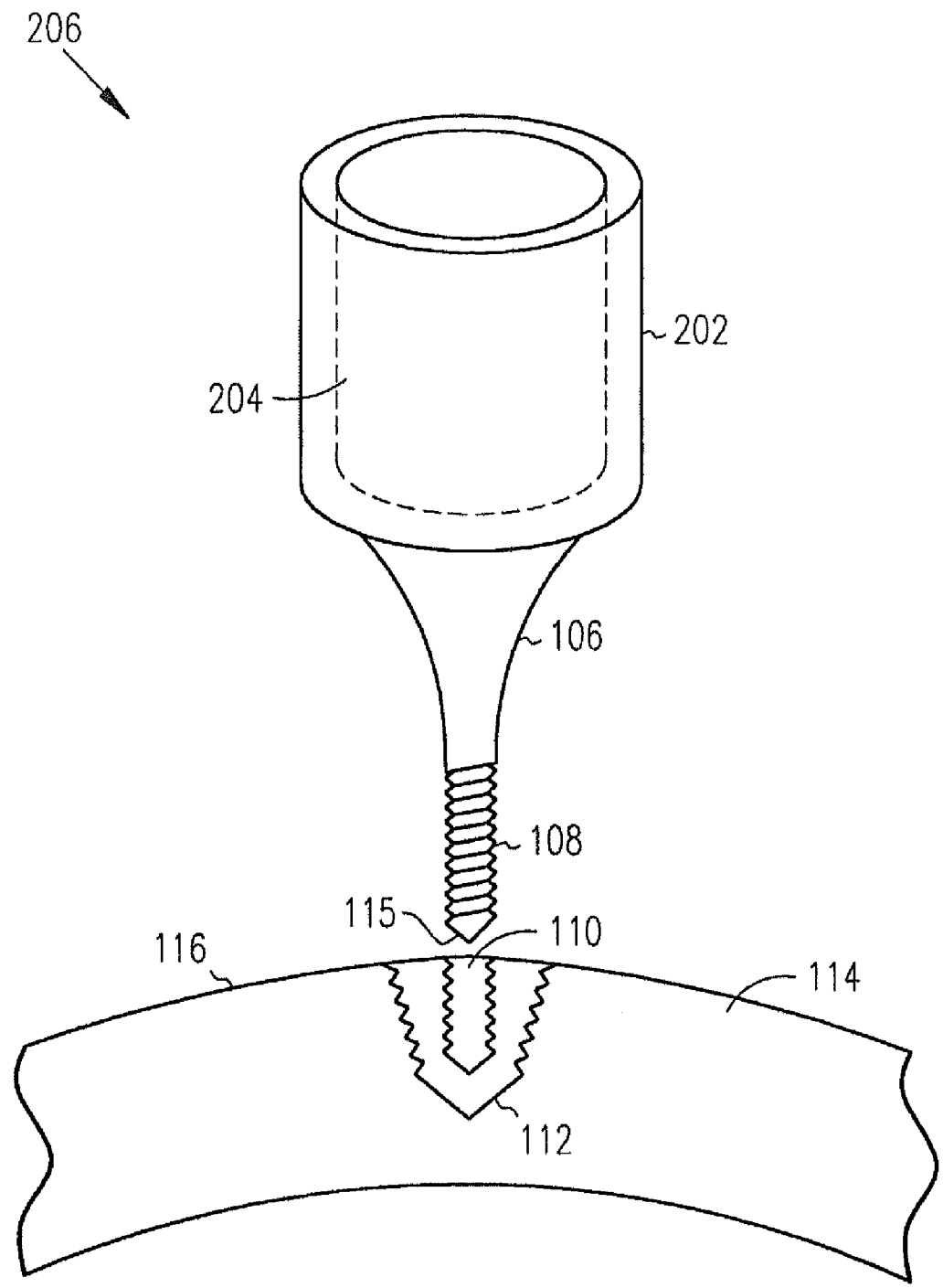
FIG. 2B is a schematic diagram illustrating generally one example of an imageable fiducial marker that omits the divot illustrated in FIG. 2A, but which is both locatable by a remote positioning system and imageable by one or more imaging modalities.

In an alternate example to the illustrations of FIGS. 1A and 2A, the divot 102 is omitted from the fiducial marker 100 or 200. However, the resulting fiducial marker is still configured to be locatable by a remote positioning system as well as imageable using one or more imaging modalities. In one such example, the outer surface 104 or 202 is still configured to be light reflective, such as discussed above. In one such example, the fiducial markers 100 and 200 still advantageously are locatable using one or more imaging modalities (e.g., MR, CT, or other imaging system providing 3D or other internal images within a subject) as well as also being locatable external to the subject, such as by using a remote camera or like component of an optical or other positioning system, e.g., that is coupled to an image-guided workstation. In one example, this permits automatic registration of the actual location of the subject in the operating room (e.g., using the cameras to locate the light reflective fiducial markers 100 or 200) to preoperative images of the patient on which the same imageable fiducial markers 100 and 200 appear. This eliminates any need to register the patient by inserting an optically-locatable positioning wand tip into a divot of each fiducial marker (and also eliminates any need for a reference divot or other absolute position reference), because the fiducial markers themselves are optically locatable and registerable to known locations on the preoperative images. Therefore, in this example, the divots 102 are not needed and can be omitted, as illustrated by the divotless spherical imageable reflective fiducial marker 120 in FIG. 1B and the divotless cylindrical imageable reflective fiducial marker 206 in FIG. 2B. Although FIG. 2B illustrates an example including a cavity 204 for carrying a liquid contrast agent, in an alternative example, the cavity 204 is omitted, and the fiducial marker 206 includes a solid structure that is doped or otherwise configured (e.g., hygroscopic) for providing good imaging contrast using one (e.g., CT) or more imaging modalities.

In yet another example, the fiducial markers 100 and 200 respectively illustrated in FIGS. 1A and 2A include the illustrated divots 102 and are locatable by a remote positioning system (such as by including light-reflective outer surfaces and/or embedded coils that perform magnetic field sensing in a magnetic field based positioning system). However, in this example, the fiducial markers 100 and 200 need not be configured for providing contrast on the one or more imaging modalities. In such an example, the preoperative images are taken with imageable fiducial markers placed within respective bases 112. Such imageable fiducial markers are then replaced (within their respective bases 112) by nonimageable fiducial markers that are locatable by a remote positioning system, such as by including both a divot and a light-reflective surface. The light reflective surface permits automatic location by the remote positioning system. However, if the reflective surface is dirty or otherwise unrecognizable by the remote positioning system, a wand or other locating instrument can be placed within the divot to perform the remote locating of the fiducial marker.

Moreover, although FIGS. 1A and 2A illustrate examples in which a shaft 106 is received within a base 112 that is mounted flush to (or recessed from) the outer surface 116 of the skull 114, this is not required. In one alternate example, the shaft 106 is manufactured as a stainless steel or other suitable material that is capable of acting as a self-tapping bone screw. In such an example, the threaded portion 108 of the shaft 106 is threaded directly into the skull 114 without using any base 112. In another alternate example, the base 112 includes a shaft or flange portion that rises above the outer surface 116 of the skull 114. In certain examples, the fiducial markers 100 and 200 may use a threaded or other shaft 106 for coupling to the base 112, or alternatively may use a snap-fit clip or a like attachment device for coupling to the base 112.

Figure 3A:
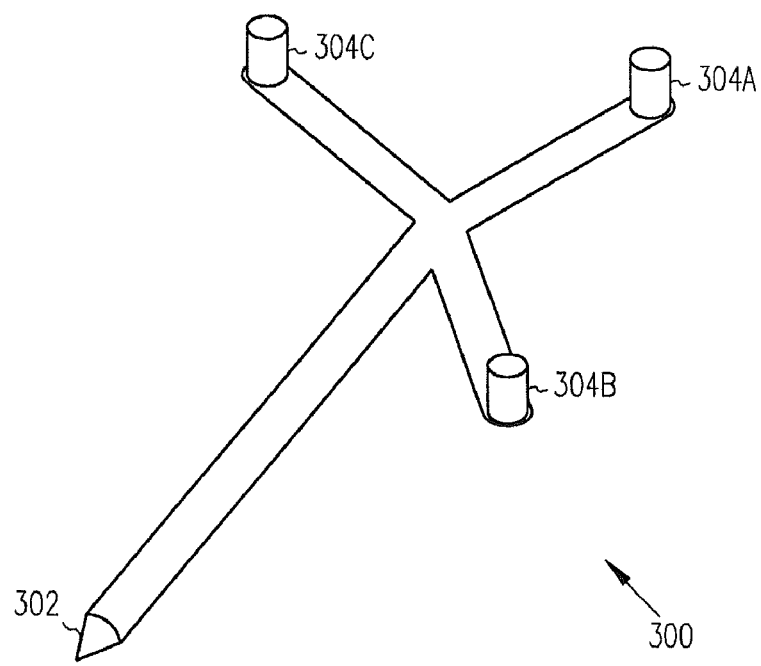
FIG. 3A is a schematic diagram illustrating generally one example of a positioning wand for use in conjunction with a remotely-located camera or other like device of an optical positioning system, such as can be coupled to an image-guided surgical workstation in an operating room.

FIG. 3A is a schematic diagram illustrating generally, by way of example, but not by way of limitation, one example of a positioning wand 300, such as for use with a remotely-located camera or other like device of an optical positioning system configured for being coupled to an image-guided surgical workstation in an operating room. In this example, the wand 300 includes a tip 302 that is sized and shaped to permit being received in a divot 102 of a skull-mounted fiducial marker (such as fiducial markers 100 and 200). The wand 300 includes a plurality of cylindrically-shaped fiducial locators 304 that are locatable by the camera or other like device of the optical positioning system. The fiducial locators 304 (which typically need not include divots) on the wand 300 are positioned in a known spatial relationship to each other and to the tip 302 of the wand 300. By recognizing the locations of the fiducial locators 304, the optical positioning system is capable of computing the location of the wand tip 302, which is in a known spatial relationship with the configuration of fiducial locators 304. This permits the wand 300 to be used in conjunction with the optical positioning system to register the patient and to further plan and/or perform the surgical procedure using the image-guided surgical workstation. The fiducial locators 304 are covered with adhesive-backed reflective tape, as discussed above. The cylindrical (or faceted cylindrical) shape of the fiducial locators 304 permits easier wrapping by the reflective tape than the spherical fiducials, as discussed above. This reduces the cost of manufacturing the fiducial locators 304 and, in turn, reduces the cost of manufacturing the positioning wand 300.

Figure 3B:
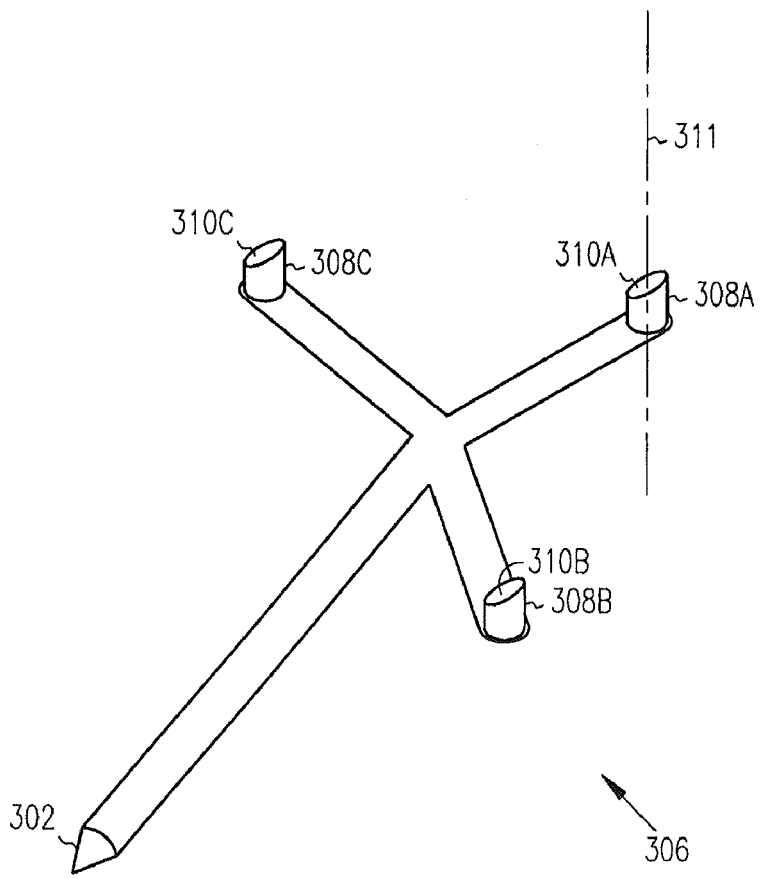
FIG. 3B is a schematic diagram, similar in certain respects to FIG. 3A, illustrating generally one example of a positioning wand including energy reflective surfaces that are capable of being oriented or aimed toward a remote detector.
Figure 3C:
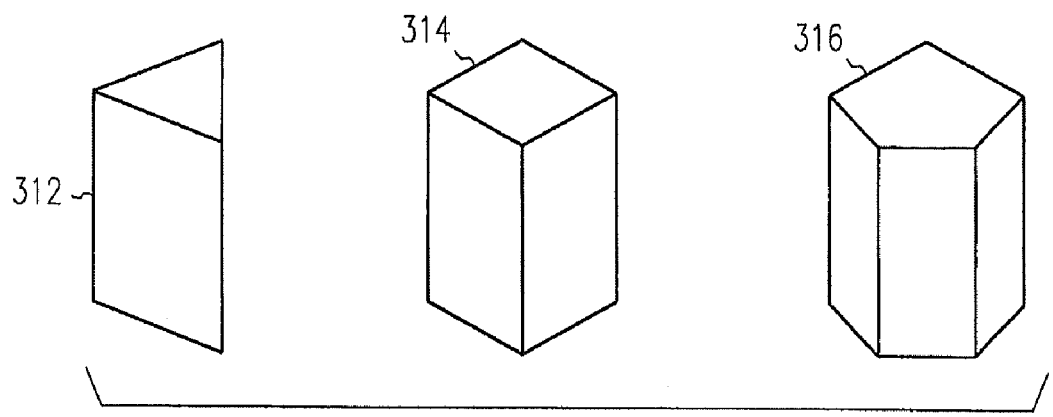
FIG. 3C is a perspective view schematic diagram illustrating generally, by way of example, but not by way of limitation, certain generally "cylindrical" columnar structures having faceted lateral peripheral surfaces.

FIG. 3B is a schematic diagram, similar in certain respects to FIG. 3A, but illustrating a wand 306 that includes locators 308A-C having swiveling or fixed cylindrical locators 308A-C having respective slanted (e.g., flat, parabolic, or other) top surfaces 310A-C (e.g., non-orthogonal with respect to a longitudinal center axis 311 of the locator 308) that reflect light or other electromagnetic energy for being located by a remote detector. In an example in which the locators 308A-C swivel, each such locator 308 includes a shaft inserted into a hole or other receptacle in the wand 306. This permits the locator 308 to rotate with respect to its mounting location on the wand 306. Either the wand 306 itself or the individual locators 308A-C are oriented by the user to aim the reflective surfaces 310A-C toward a camera or other detector of an optical positioning system. In one further example, the circumferential surfaces of the cylindrical locators 308A-C are also light-reflective, however, this is not required. In one such cost-effective example, the reflective tape disks are adhered to the flat slanted top surfaces 310A-C and the circumferential lateral surfaces of the cylindrical locators 308A-C are not reflective.

FIG. 3C is a perspective view schematic diagram illustrating generally, by way of example, but not by way of limitation, certain generally "cylindrical" columnar structures 312, 314, and 316 having faceted lateral peripheral surfaces. Such surfaces are conducive to receiving a rectangular or like strip of adhesive reflective tape. Such structures, therefore, are particularly well-suited for implementing locators that are remotely locatable by an optical positioning system. Such remotely detectable locators are suitable for use in the fiducial markers illustrated in FIGS. 2A and 2B, as well as for use in the remotely detectable locators of the positioning wands illustrated in FIGS. 3A and 3B. Such remotely detectable locators are also useful for being affixed in a known relationship to the patient, such as to the operating table or to a skull-immobilizing headframe. This provides a remotely detectable absolute positional reference to an optical positioning system. Such remotely detectable locators are also useful for being affixed to a biopsy needle, shunt catheter, or other instrument being introduced through a trajectory guide device or otherwise used in an image-guided surgical procedure.

Figure 3D:
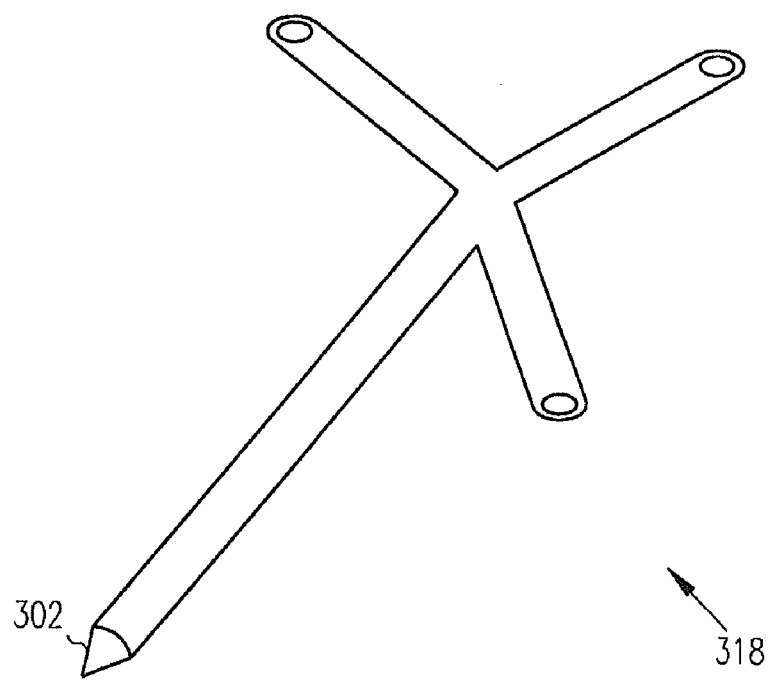
FIG. 3D is a schematic diagram illustrating generally an example of a positioning wand with flat disk-shaped pieces of reflective tape are attached in a known configuration.

FIG. 3D is a schematic diagram illustrating generally, by way of example, but not by way of limitation, an alternative example of a positioning wand 318. In this example, which flat disk-shaped pieces of reflective tape are attached to the wand 318 in a known configuration, such as at the distal ends of radial arms extending therefrom.

Example 2

Figure 4:
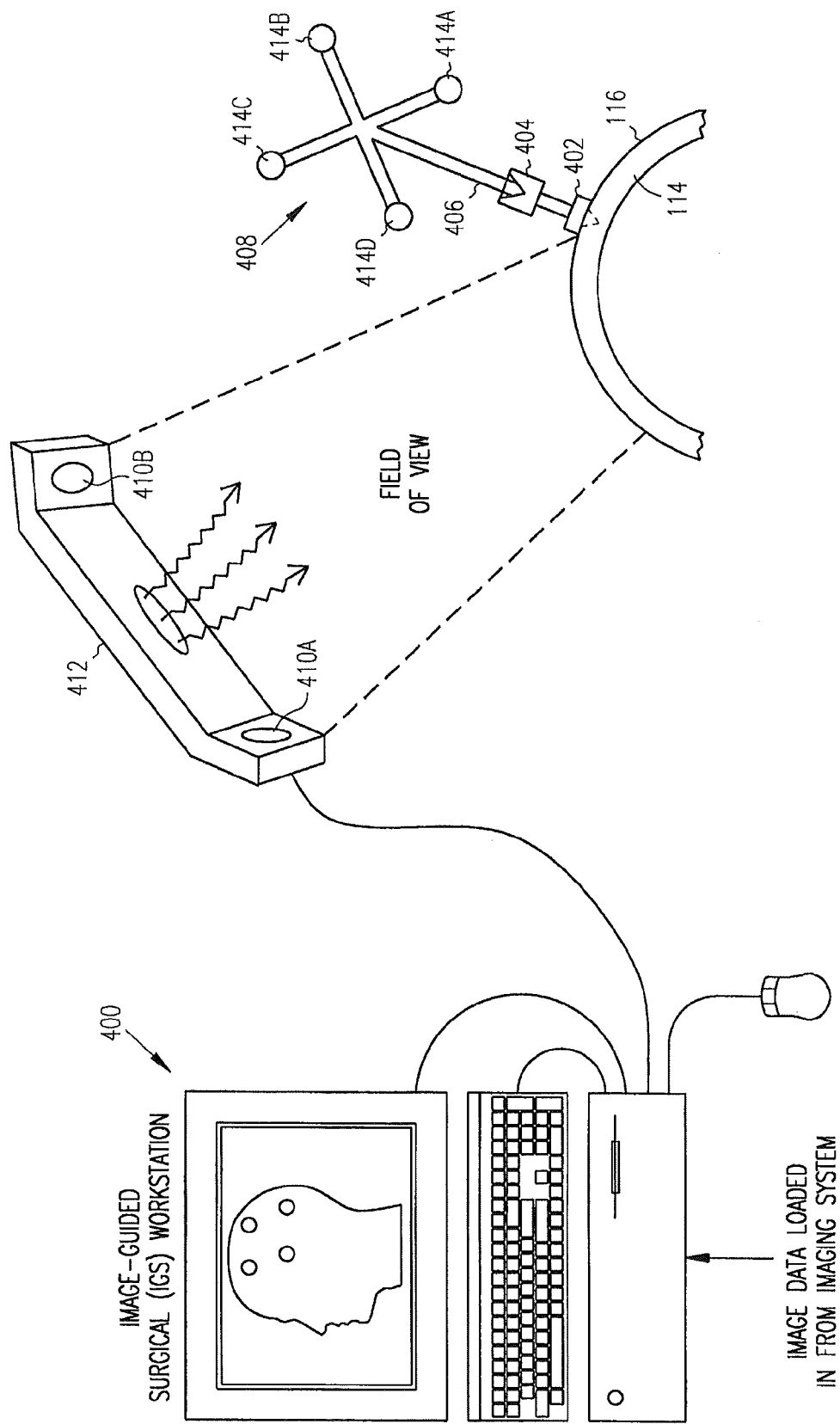
FIG. 4 is a schematic diagram illustrating generally, by way of example, but not by way of limitation, an image guided surgical (IGS) computer workstation to which an optical positioning system is coupled.

FIG. 4 is a schematic diagram illustrating generally, by way of example, but not by way of limitation, an image guided surgical (IGS) computer workstation 400, which is capable of displaying previously acquired and loaded preoperative images of a patient's skull. On these preoperative images appear viewable images of imageable fiducial markers that were screwed into the patient's skull before the preoperative imaging (e.g., using MRI, CT, etc.). In the example illustrated in FIG. 4, the imageable fiducial locators have been unscrewed from respective bases 402 screwed into the patient's skull. The imageable fiducial locators have been replaced by patient registration divot assemblies 404 that have been screwed into (or otherwise coupled to) respective bases 402 in the patient's skull 114. In this example, the registration divot assemblies 404 are configured to receive a shaft tip 406 of a positioning wand 408 that is locatable by one or more remote cameras 410A-B (or other sensing devices) of an optical position detection system 412 connected to the IGS workstation 400. In one example, the positioning wand 408 includes spherical reflective fiducial locators 414. The fiducial locators 414 are arranged in a known spatial relationship to each other (however, it may alternatively use other reflective locators such as discussed elsewhere in this document). The optical positioning system 412 includes an infrared light (or other energy source) 416 that provides light that is reflected from the reflective fiducial locators 414. This permits the reflective fiducial locators 414 on the positioning wand 408 to be located and recognized by the cameras 410A-B. In some circumstances, however, the field of view (or "sweet spot" of the field of view) provided by cameras 410A-B is limited. This sometimes makes it difficult for the optical positioning system 412 to recognize the positioning wand 408. Moreover, the recessed receptacle in the divot assembly 404 typically limits the range within which the probe 408 can be manipulated (e.g., to bring it within the field of view) while retaining the wand tip 406 within the recessed receptacle.

Figure 5:
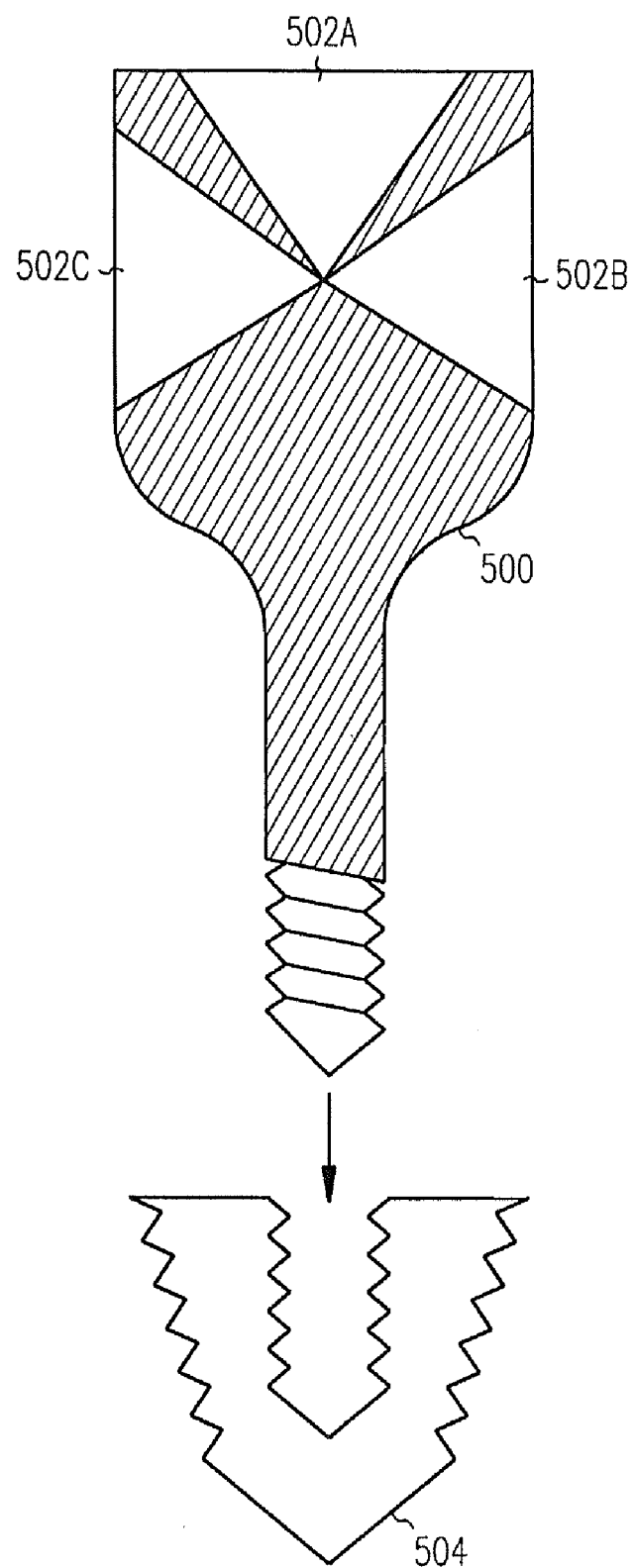
FIG. 5 is a schematic diagram illustrating generally a unitary divot assembly that includes multiple divots.

FIG. 5 is a schematic diagram illustrating generally, by way of example, but not by way of limitation, a unitary divot assembly 500 that includes multiple divots 502. In this example, the unitary divot assembly 500 is configured such that it can be threaded into or otherwise coupled to a base 504 that is secured to the patient's anatomy (wherein the base 504 is also configured for alternatively receiving an imageable fiducial locator, e.g., during preoperative imaging). FIG. 5 illustrates multiple conical receptacle divots 502 having commonly located apexes. These commonly located apexes are designed to coincide with the center of the image produced by the imageable fiducial locator for which the divot assembly 500 has been substituted during patient registration. In the illustrated example, the divots include a top conical divot 502A and four side conical divots 502B-F. The four side conical divots 502B-F are distributed around the cylindrical lateral peripheral circumference of the upper portion of the divot assembly 500. The wand tip 406 may be inserted into any one of the divots 502. This permits a greater range of motion of the positioning wand 408. As a result, it is easier to bring the reflective fiducials 414 on the positioning wand 408 into the field of view of the cameras 410A-B of the optical positioning system 412.

Figure 6A:
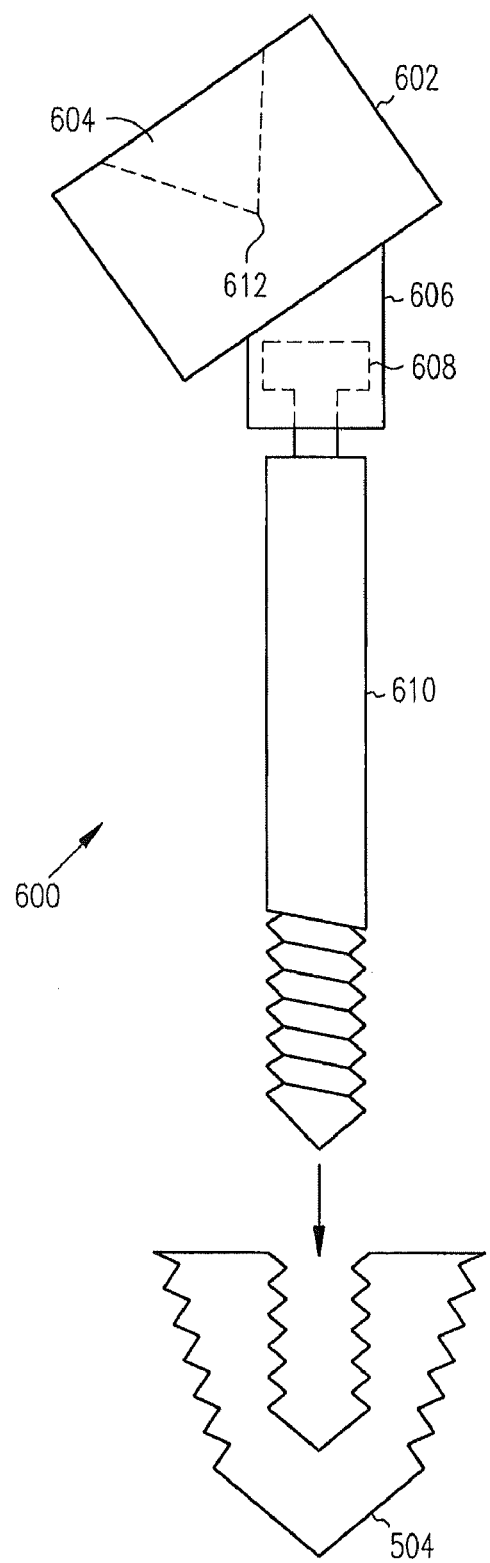

FIG. 6A is a schematic diagram illustrating generally, by way of example, but not by way of limitation, a divot assembly 600 that includes a swiveling tilted head 602 carrying a conical or other divot 604 or the like. In this example, the head 602 is tilted with respect to a cylindrical coupling 606 extending outwardly therefrom. The coupling 606 includes a hollow interior or other (female or male) connector that snap-fits onto and rotatably rides upon a mating (male or female) connector 608 that is located at a proximal end of a shaft 610 portion of the divot assembly 600. The swiveling apex 612 of the divot 604 is designed to coincide with the center of mass of the imageable fiducial locator for which the divot assembly 600 has been substituted during patient registration. The swiveling tilted head 602 permits a wide range of motion of the positioning wand 408 when the wand tip 406 is inserted into the divot 604. As a result of such rotational articulation, it is easier to bring the reflective fiducial locators 414 on the positioning wand 408 into the limited field of view of the cameras 410A-B of the optical positioning system 412.

Figure 7A:
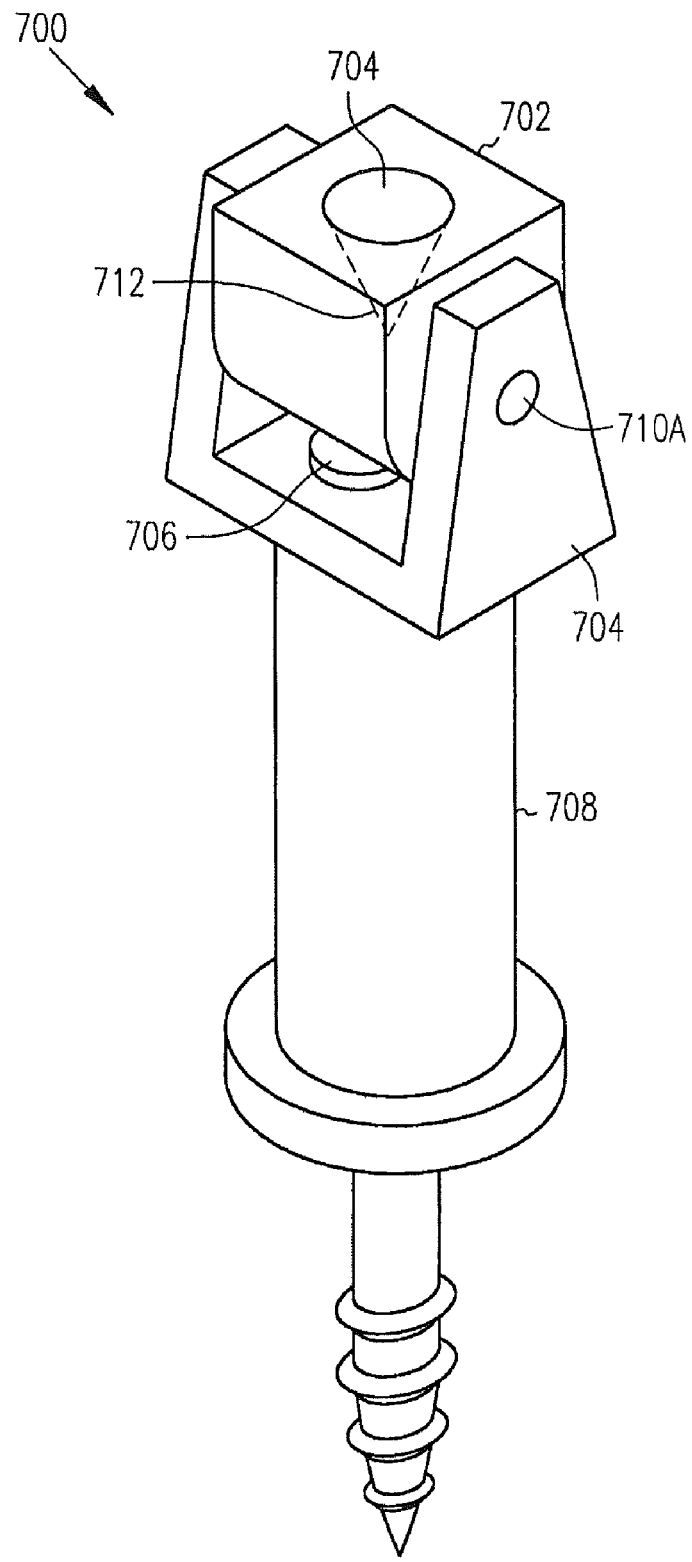
FIG. 7A is a schematic diagram illustrating generally a divot assembly that includes a swiveling and pivotable head carrying a conical or other divot.

FIG. 7A is a schematic diagram illustrating generally, by way of example, but not by way of limitation, a divot assembly 700 that includes a swiveling and pivotable head 702 carrying a conical or other divot 704. In this example, the head 702 is carried by a shackle-like U-shaped bracket 704 that rotatably rides upon a snap-fit or other capturing post 706 that extends upward from a shaft portion 708 of the divot assembly 700. This allows swiveling of the bracket 704 (and the head 702 carried by the bracket 702) with respect to the shaft 708. In this example, the head 702 is suspended between upward-projecting risers of the bracket 704 by axels 710A-B extending outward from opposing sides of the head 702 and received within corresponding receptacles in the risers of the bracket 704. This permits pivoting/tilting articulation of the head 702 with respect to the swiveling bracket 704. Therefore, this example provides a swiveling and adjustably tiltable divot 704 that is designed such that its apex 712 coincides with the center of mass of the imageable fiducial locator for which the divot assembly 700 has been substituted during patient registration. Among other things, the swiveling tiltable head 702 advantageously permits a greater range of motion of the positioning wand 408 when the wand tip 406 is inserted into the divot 704. As a result, it is easier to bring the reflective fiducials 414 on the positioning wand 408 into the limited field of view of the cameras 410A-B of the optical positioning system 412.

Figure 6B:
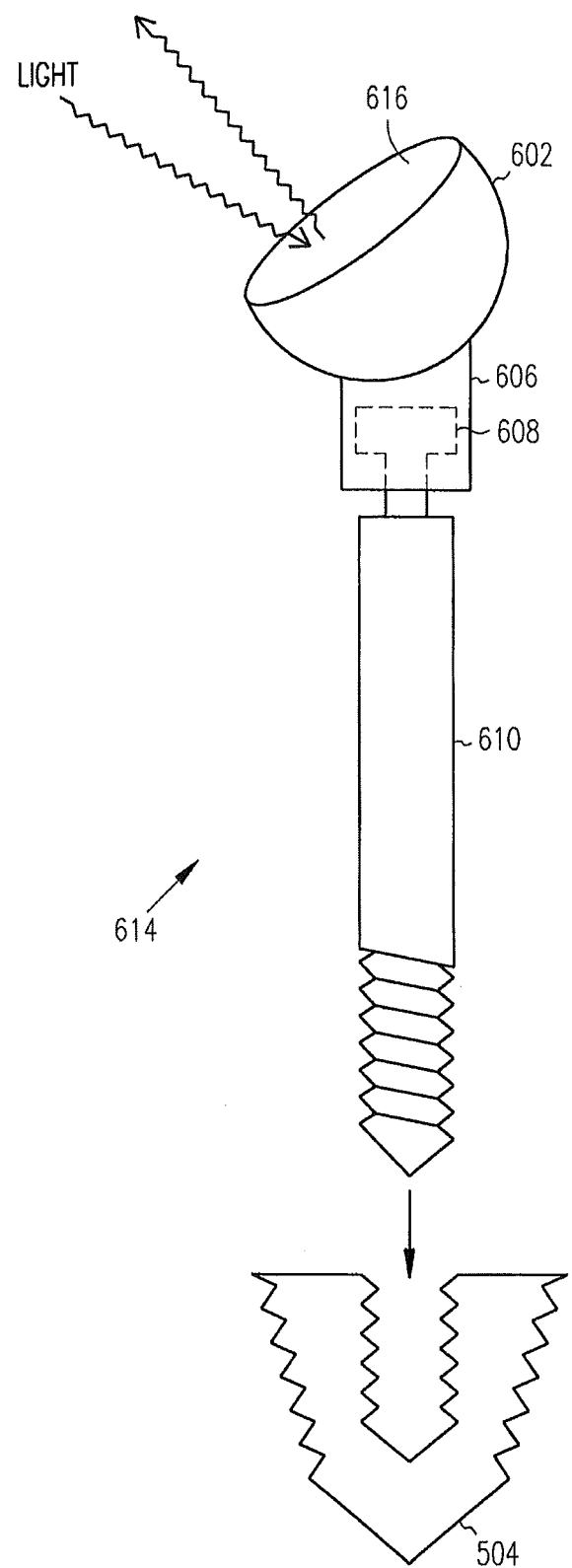
FIG. 6B is a schematic diagram illustrating generally a locator assembly that includes a swiveling tilted head including a surface that reflects electromagnetic energy.
Figure 7B:
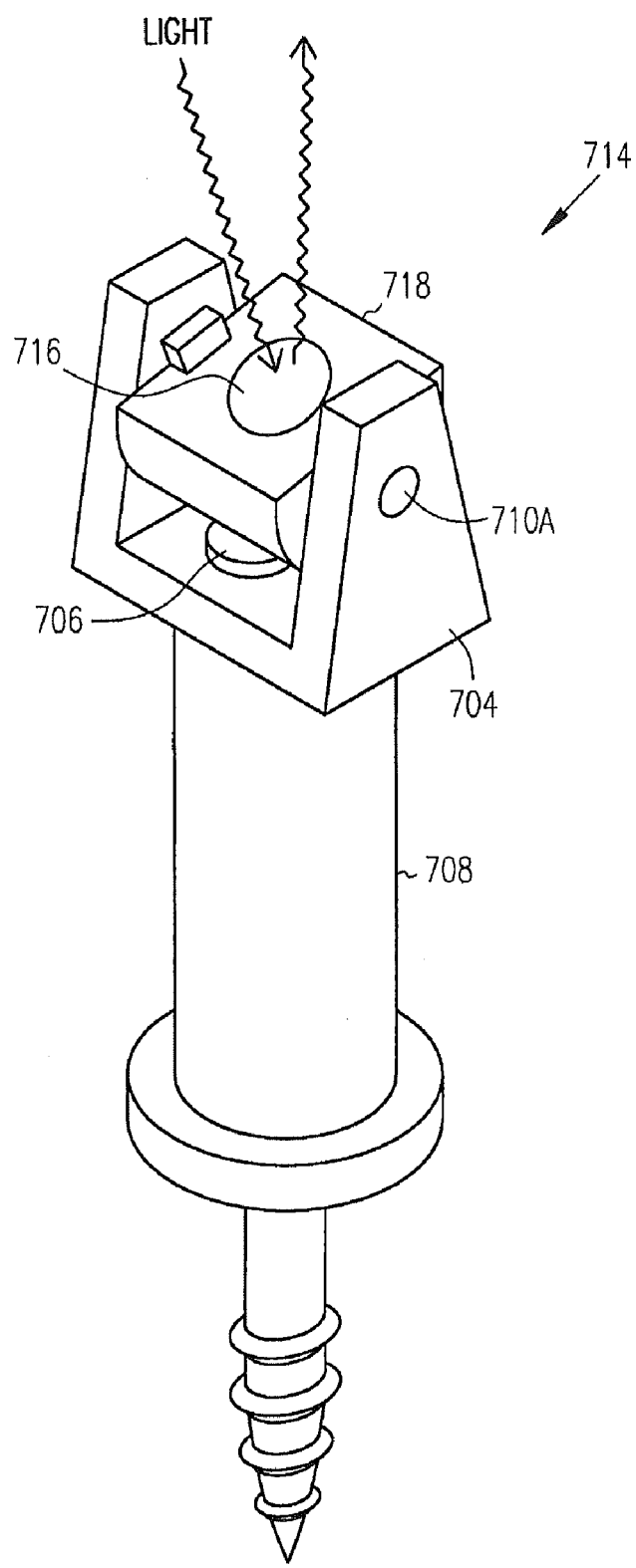
FIG. 7B is a schematic diagram illustrating generally a divot assembly that includes a swiveling and pivotable head including a surface that reflects electromagnetic energy.

FIGS. 6B and 7B are schematic diagrams that are similar in certain respects to FIGS. 6A and 7A. However, the locator assemblies 614 and 714 illustrated by respective FIGS. 6B and 7B omit the respective divots 604 and 704. Instead, the locator assemblies 614 and 714 provide aimable electromagnetic energy (e.g., light) reflective surfaces 616 and 716, respectively. The reflective surfaces 616 and 716 are aimed at the camera of an optical positioning system 412 to allow automatic detection of the locator assemblies 614 and 714 without requiring the use of a positioning wand 408.

The reflective surfaces 616 and 716 are configured so that, when aimed properly, they produce a reflected image that can be correlated to a previously acquired patient image on which an image of an imageable fiducial marker appears. In one such example, reflective surface 616 corresponds to the center of mass of a similarly sized spherical locator on an imageable fiducial marker assembly for which locator assembly 614 is substituted during patient registration. In another such example, reflective surface 716 includes a circular disk-shaped piece of reflective tape affixed to a surface 718 such that this reflective disk pivots about the axis provided by axels 710A-B. In this manner, the reflected disk shape corresponds to the center of mass of a similarly sized spherical locator on an imageable fiducial marker assembly for which locator assembly 714 is substituted during patient registration.

Example 3

Figure 8:
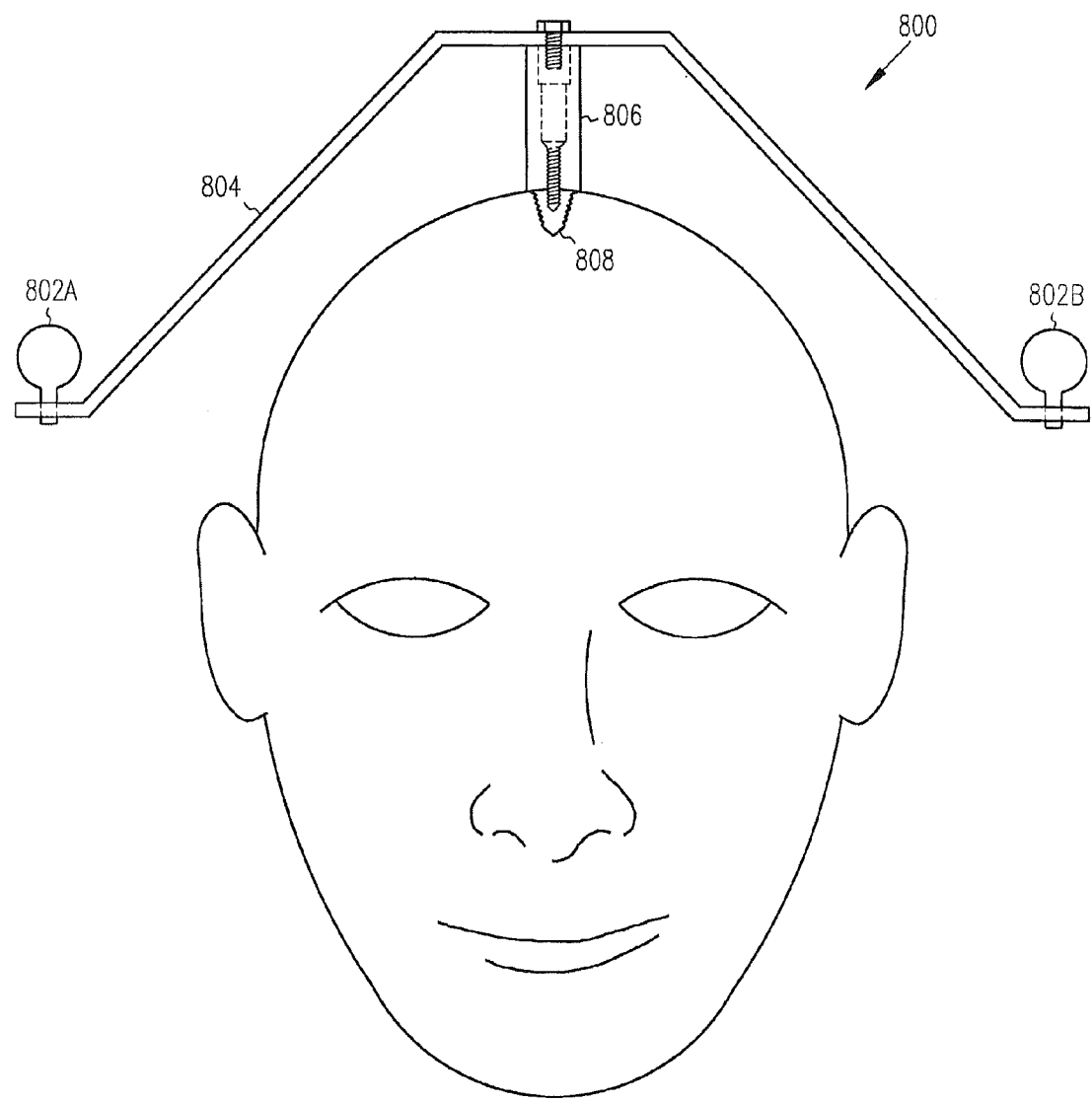
FIG. 8 is a schematic diagram illustrating conceptually a fiducial marker carrier that is attachable to (and also detachable from) a single location on the patient's skull, thereby reducing trauma to the patient.

As discussed above, screwing multiple fiducial markers into different locations in the patient's skull 114 results in trauma and/or risk of infection at each one of such multiple different locations. FIG. 8 is a schematic diagram illustrating conceptually, by way of example, but not by way of limitation, a fiducial marker carrier 800 that is attachable to (and also detachable from) a single location on the patient's skull 114, thereby reducing trauma and risk of infection to the patient. In this example, the fiducial marker carrier 800 is configured for carrying multiple different imageable fiducial locators 802 such that they are positioned at different locations about the patient's skull 114. As discussed below, the carrier 800 uses a keyed mounting arrangement, such that the carrier 800 can be attached to the patient's skull 114, then detached from the patient's skull 114, and later reattached to the patient's skull 114 in the same orientation in which it was initially attached to the patient's skull 114.

In the example illustrated in FIG. 8, the carrier 800 includes a keyed frame 804 that is attached to a keyed post 806 for mounting. The keyed post 806 is, in turn, attached to a single flush-mounted or recessed-mounted or other keyed base 808, which was previously screwed into the patient's skull 114. This keyed arrangement of the frame 804, the post 806, and the base 808 permits attachment, detachment, and reattachment in the same orientation as the original attachment, as discussed above. In an alternative example, the post 806 is integrally formed as part of the frame 804, rather than being keyed for attachment thereto.

In one example, such illustrated in FIG. 8, the imageable locators 802 are placed about the subject's head such that they surround the patient's skull. Although such a surrounding arrangement is not required, it is believed to improve the accuracy of using the images of the locators 802 (e.g., in conjunction with the IGS workstation) for planning and/or performing an image-guided surgical procedure, as compared to an arrangements in which locators are disposed more closely together (e.g., on the same side of the subject's head).

Figure 9:
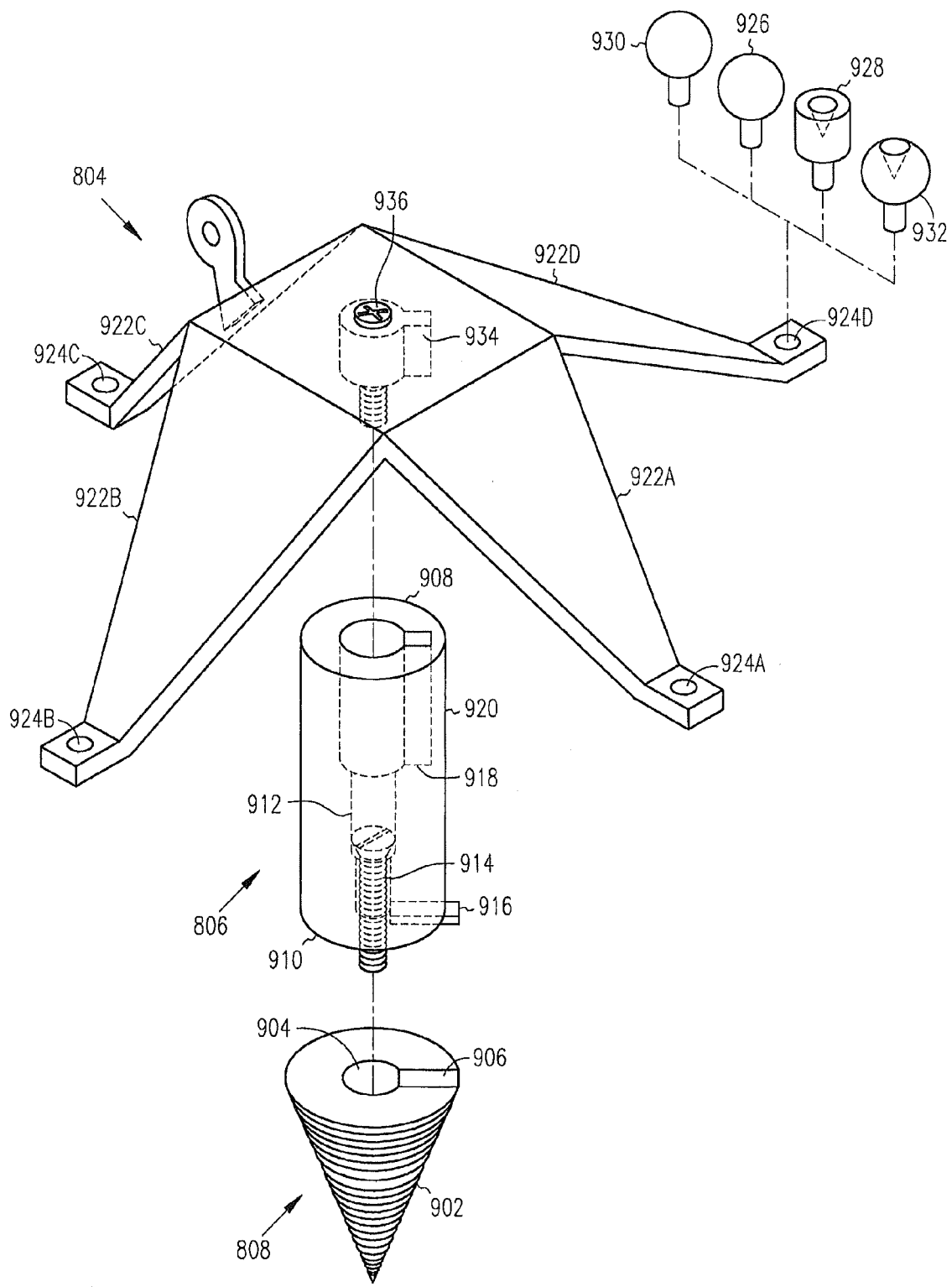
FIG. 9 is an exploded view schematic diagram illustrating generally one example of the carrier, including a frame, a post, and a base.

FIG. 9 is an exploded view schematic diagram illustrating generally, by way of example, but not by way of limitation, one example of the carrier 800, including the frame 804, the post 806, and the base 808. In this example, the base 808 includes self-tapping external threads 902, and is capable of being mounted flush with (or even recessed within) the patient's skull 114. The base 808 includes an internally-threaded receptacle 904 that is sized and otherwise configured such that it is capable of receiving a screw. The base 808 also includes a female or male keying feature for receiving a mating keying feature of the post 806 to fixedly define the orientation of the post 806 with respect to the base 808. In one example, the keying feature includes a key slot 906 extending radially outward from the receptacle 904 along a proximal surface of the base 808.

The post 806 includes a proximal end 908 and a distal end 910. The post 806 includes a center lumen 912 in which an attachment screw 914 is received and seated. The screw 914 attaches the post 806 to the base 808. The distal end 910 of the post 806 includes a male or female keying feature (such as a key protrusion 916 extending radially outward from the center lumen 912 along the distal end 910 of the post 806) that mates with the keying feature (e.g., key slot 906) of the base 808. Such mating during the attachment fixedly defines the orientation of the post 806 with respect to the base 808.

In this example, the center lumen 912 includes a keyed seating receptacle 918 (or an analogous male keyed feature) for receiving a mating keyed feature of the frame 804. In the illustrated example of FIG. 9, the keyed seating receptacle 918 includes an increased diameter of the center lumen 912 (with respect to more distal portions of the center lumen 912) to provide the seating, and a radially-outwardly extending slot 920 to provide the keying.

In the example illustrated in FIG. 9, the frame 804 includes legs 922A-D (or a fewer or greater number of legs 922), such as extending radially outwardly from a hub 924 and downwardly toward the middle portion of the patient's skull. Each of the legs 922 includes, such as at its respective distal end, a threaded receptacle 924A-D (or a snap-fitting or any other coupling) for receiving at least one of an imageable fiducial marker assembly 926, a divot assembly 928, a locator assembly 930 (e.g., reflector, LED, microcoil, etc.) that is remotely detectable by a positioning system in an operating room, or a combination 932 of two or more of the above. In an alternative embodiment (for example where a combination 932 includes an imageable locator and at least one of an operating room position locator and a divot), instances of such a combination 932 may be permanently affixed to corresponding locations on the legs 922 of the frame 804.

In the example illustrated in FIG. 9, the hub 924 portion of the frame 804 also includes a downwardly protruding key 934 (or analogous female receptacle) that mates to the keyed seating receptacle 918, of the post 806, into which the key 934 is received. This fixedly defines the orientation of the frame 904 with respect to the post 806. A screw 936 is inserted through the hub 924, the key 934, and into an engaging interior threaded portion of the center lumen 912. This securely attaches the frame 904 to the post 806 in the fixedly defined orientation. The example illustrated in FIG. 9 also includes at least one optional instrument mount 938. In one example, a reference divot (e.g., providing a position reference) is attached to the instrument mount 938.

Although FIGS. 8 and 9 illustrate examples in which a fiducial marker carrier 800 is mounted using a single base 808, in other examples, the carrier may be mounted using two or more bases 808 at the same location on the patient's skull (that is, at adjacent locations within the same scalp incision, or like limited trauma/infection risk zone; the incision need only be large enough to accommodate the two or more bases 808). Using two or more side-by-side bases 808 to attach the post 806 avoids potential rotational misalignment of a single base 808 coming slightly unscrewed from its original position.

Figure 10:
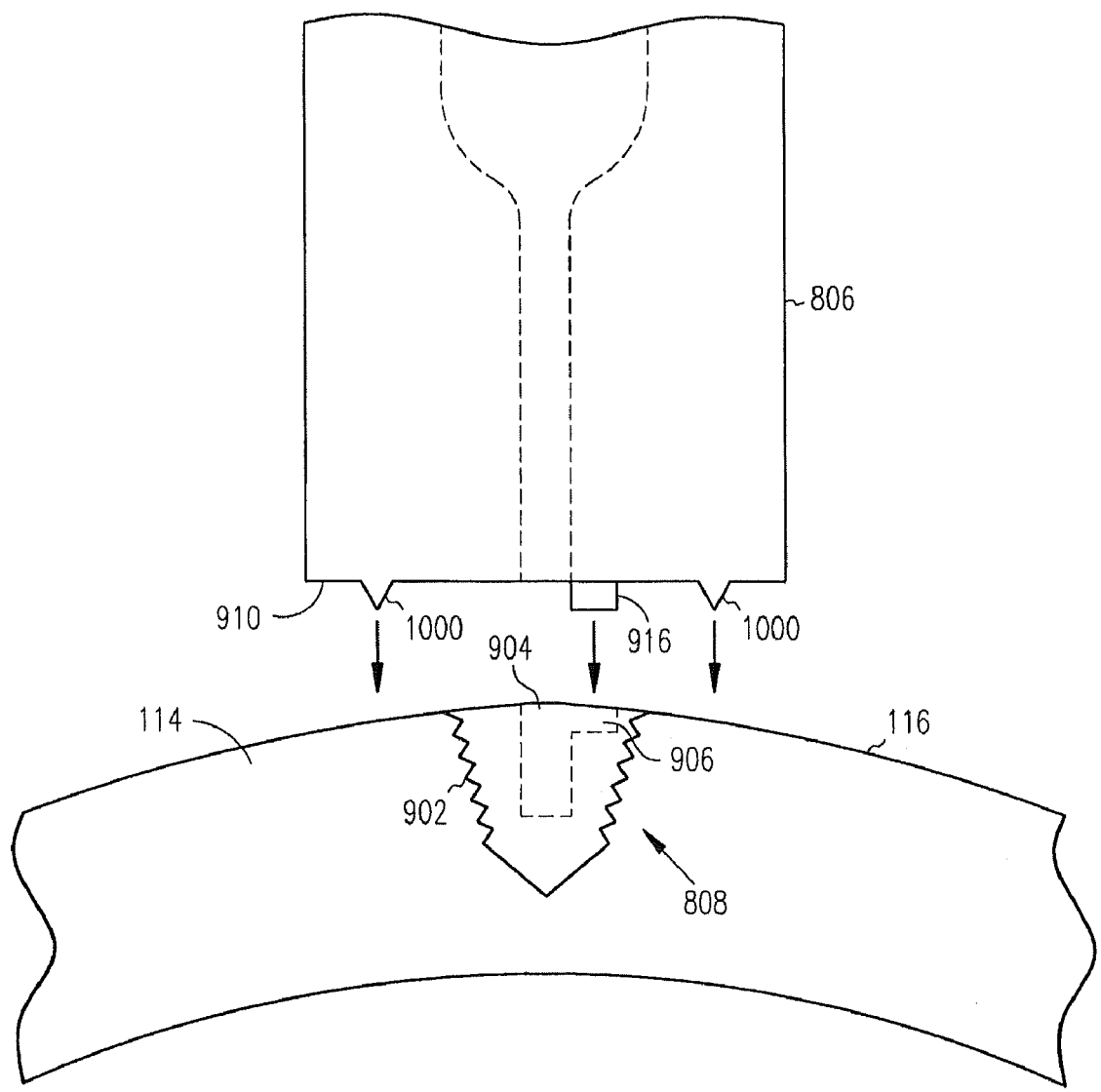
FIG. 10 is a schematic diagram illustrating a portion of a fiducial marker carrier that includes at least one antirotational spike for engaging the surface of the skull.

Alternatively, if a single base 808 is used, such rotational misalignment can be avoided by including one or more antirotation spikes 1000 on the bottom of the distal end 910 of the post 806, such as illustrated generally in FIG. 10. In the example illustrated in FIG. 10, the distal end 910 of the post 806 is keyed both to the base 808 and, using the antirotation spike(s) 1000, to indentation(s) made in the surface 116 of the skull 114. However, in an alternative example, the post 806 and the base 808 need not be keyed to each other. Instead, in such an example, the post 806 is keyed only to indentation(s) made by the antirotation spike(s) 1000 in the surface 116 of the skull 114.

Example 4

Figure 11:
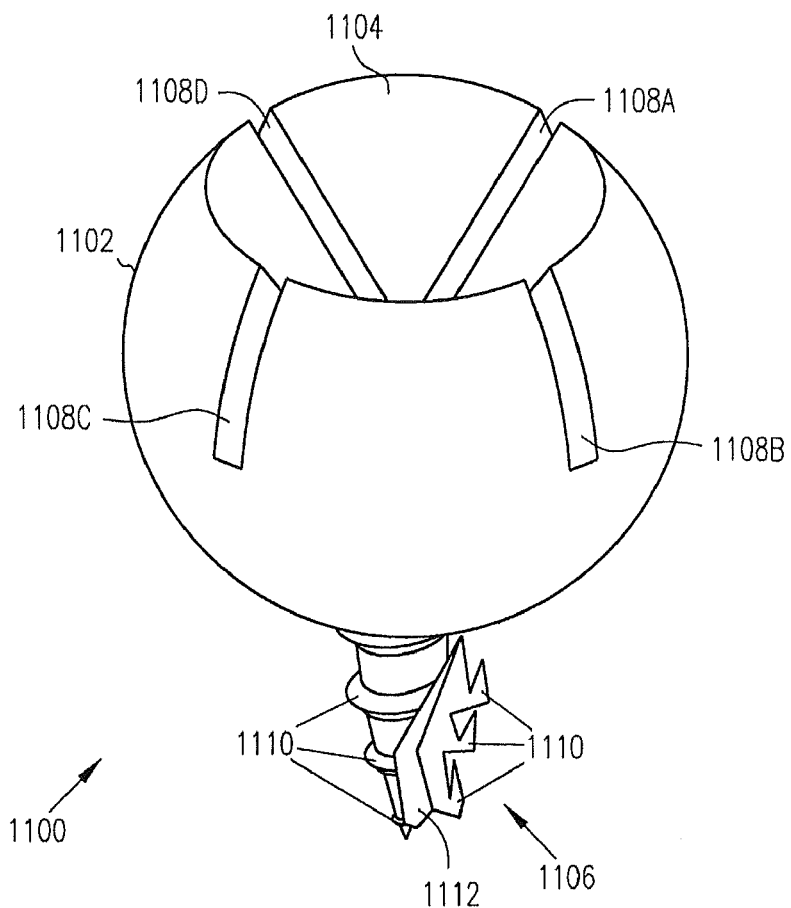
FIG. 11 is a perspective view of an alternative example of a fiducial marker.
Figure 12:
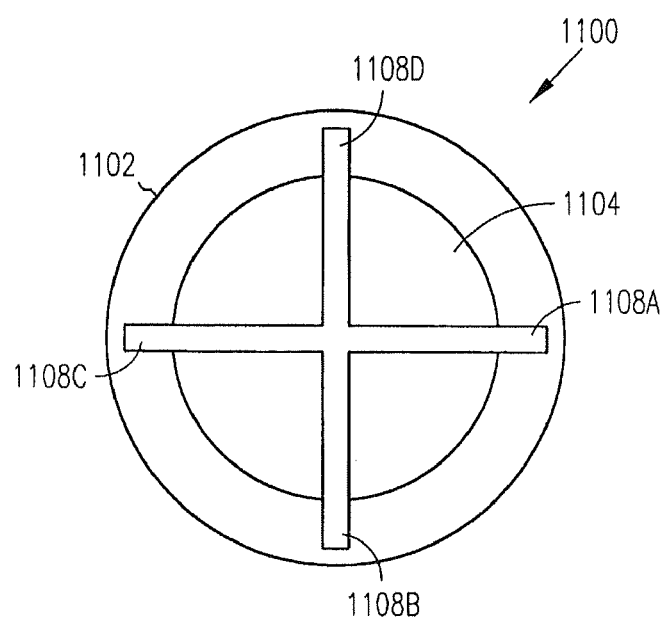
FIG. 12 is a top view of the fiducial marker illustrated in FIG. 11.

FIG. 11 is a perspective view of an alternative example of a fiducial marker 1100. FIG. 12 is a top view of the fiducial marker 1100 illustrated in FIG. 11. In the example of FIGS. 11-12, the unitary fiducial marker 1100 includes a substantially spherical head 1102. A unitary fiducial marker includes both a single piece as well as multiple pieces that are assembled into a single assembly that, in use, is not disassembled or otherwise decomposed into more than one separate component. In this example, a divot 1104 is cut out from a proximal portion of the head 1102. The divot 1104 is shaped to receive a corresponding mating shaped portion of a remote positioning locator. In one illustrative example, the divot 1104 is conical (as illustrated in FIG. 11), such as to receive a mating conical tip 302 of the positioning wand 300 illustrated in FIG. 3, or a similar probe tip. An apex of the inverted conical divot 1104 corresponds to a centroid of the substantially spherical head 1102. In this example, a bone screw shaft 1106 extends outward from an opposite (e.g., distal) portion of the head 1102. (Alternatively, if a sterile drape or the like is to be used between the tip 302 of the wand 300 and the divot 1104 of the fiducial marker 1100, then, in one example, the location of the apex of the divot 1104 may be adjusted to offset the thickness of the sterile drape such that the tip 302 of the wand 300 is located at the centroid of the head 1102 even when the drape is interposed between the tip 302 and the divot 1104).

In this example, the conical divot 1104 of the head 1102 includes slots 1108 extending therefrom. The slots 1108 accommodate a driving tip of a screwdriver (e.g., Phillips and/or flathead, etc.). In this manner, the slots 1108 permit the fiducial marker 1100 to be screwed into a skull, bone, or other structure. Alternatively, the divot 1104 includes any other known rotational engagement structure for permitting rotation of the fiducial marker 1100 for threading it into bone, as discussed below.

In one example, the shaft 1106 includes one or more self-tapping or other external bone screw threads 1110, which are sized and shaped for being threaded into bone, such as a patient's skull. In one example, a distal tip of the shaft 1106 includes at least one cutout, such as a quarter cylindrical cutout 1112. In this example, the vertically-oriented flute-like cutout 1112 portion of the shaft 1106 assists in cutting bone as the shaft 1106 is being turned for threading into the bone. The self-drilling cutout 1112 and self-tapping nature of the threads 1110 are not essential. These features are not needed, for example, where a pre-drilled hole is available and used for receiving the shaft 1106.

In one example, the unitary fiducial marker 1100 is made from substantially pure or alloyed titanium, substantially pure or alloyed stainless steel, and/or a ceramic. In one example, the resulting substantially spherical head 1102 is radiolucent and/or radiographically imageable and viewable using computed tomography (CT).

In the example of FIG. 11, the unitary fiducial marker 1100 includes an imageable locator head 1102 that is spherical (or otherwise shaped) for obtaining accurate location information (e.g., of its center). The head 1102 also includes a receptacle (such as the divot 1104) that is shaped for receiving a mating portion (e.g., tip 302) of a positioning instrument (e.g., wand 300) during patient registration. Therefore, the unitary fiducial marker 1100 (with integrated imaging and registration divot) in the example of FIG. 11 avoids having to replace an imageable portion of a two-piece fiducial marker (used during preoperative imaging) with a separate registration divot (used during patient registration in the operating room). This simplifies an image-guided surgical procedure using the unitary fiducial marker 1100 having both the imageable head 1102 and the integrated divot 1104. Such simplification should help lower the cost of the image-guided surgical procedure.

Figure 13:
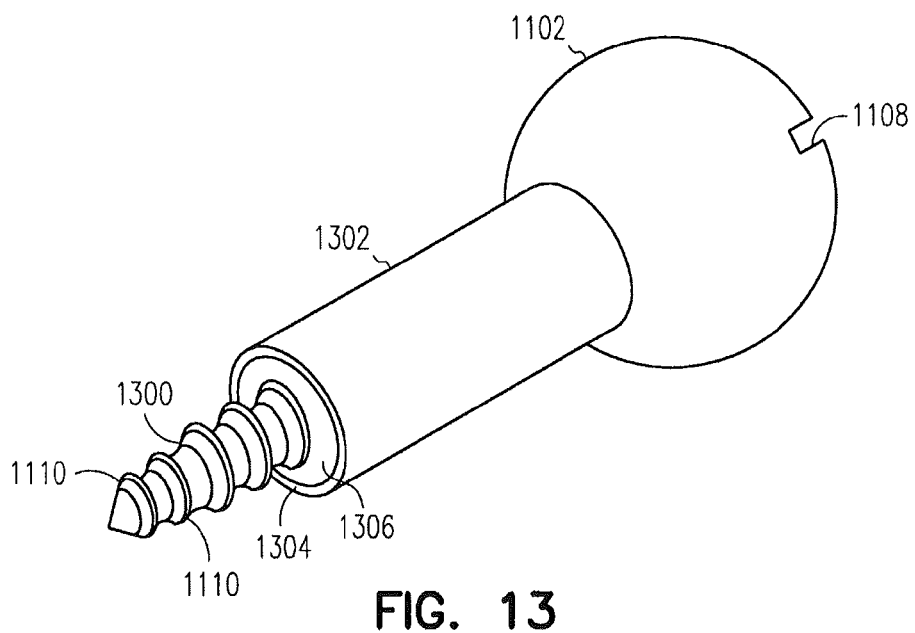
FIG. 13 is a perspective view of modified unitary fiducial marker.

FIG. 13 is a perspective view of modified unitary fiducial marker 1100. In this example, the shaft 1106 includes a threaded distal portion 1300 and an unthreaded proximal portion 1302. The unthreaded proximal portion 1302 distances the head 1102 from the surface into which the threaded distal portion 1300 is screwed. In this example, the unthreaded proximal portion 1302 of the shaft 1106 is of a larger cylindrical diameter than the tapered threaded distal threaded portion 1300 of the shaft 1106. This forms a circular shoulder or seat 1304 at the base of the unthreaded proximal portion 1302 where it meets the threaded distal portion 1300. When the seat 1304 is of a larger diameter than the major diameter of the threads 1110, the seat 1304 provides a shoulder acting as a depth stop that inhibits the fiducial marker 1100 from being further advanced into the bone, such as by an accidental impact to the head 1102 of the fiducial marker 1100 that produces a mechanical shock.

In one example, several fiducial markers 1100 are packaged and sold together as a kit. In one such example, such a kit includes two or more different fiducial markers 1100 having different lengths of the unthreaded proximal portion 1302 of their respective shafts 1106. This accommodates patients having different skin or scalp thicknesses. For example, it may be desirable to keep the head 1102 portion of the fiducial marker 1100 above the patient's skin or scalp, while remaining as close to the skull as possible. If this is desired, it can be accomplished by selecting from the kit a particular fiducial marker 1100 having an appropriate shaft 1106 length to accommodate the skin or scalp thickness of the patient.

In this example, the seat 1304 includes a circular groove, channel, or kerf 1306. In this example, the kerf 1306 extends along the seat 1304 circumferentially around the threaded distal portion 1300. The kerf 1306 accommodates therein loose bone fragments that are channeled upward by the threads 1110 when the fiducial marker 1100 is being screwed into the skull. Such groove, channel, or kerf 1306 for accommodating channeled bone fragments could similarly be incorporated into a distal side of the head 1102 in the examples of FIGS. 10-11, in which the threaded portion of the shaft 1106 extends directly from the head 1102.

Example 5

Figures 14, 15:
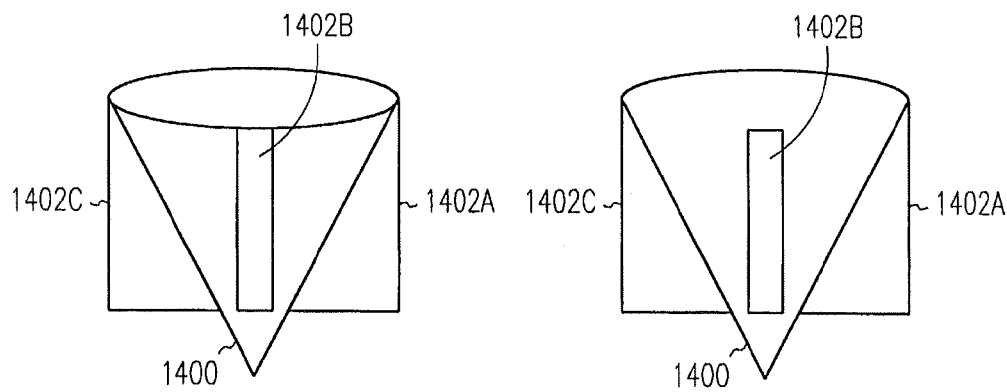
FIG. 14 is a perspective view of an optional imageable plug.
FIG. 15 is a side view of the optional imageable plug of FIG. 14.

FIG. 14 is a perspective view of an optional imageable plug 1400. FIG. 15 is a side view of the optional imageable plug 1400, which can be made from the same material as the head 1102, if desired. The imageable plug 1400 is sized and shaped to be inserted into the divot 1104 during imaging such that the head 1102 presents a uniformly shaped imageable sphere to the imaging modality. This assists in easier location of the centroid of the spherical combination of the head 1102 and the plug 1400, but is not believed to be required. In this example, the imageable plug 1400 is then removed during registration, thereby permitting access to the divot 1104. In one example, the plug 1400 includes fins 1402 that are sized and shaped for engaging the corresponding slots 1108. In an alternative example, however, the fins 1402 are omitted.

In an alternative example, the imageable plug 1400 is made from a material having a slightly or substantially different imaging contrast property from the material comprising the rest of the head 1102. In this manner, an image of the fiducial marker can be obtained in which the divot 1104 appears with a different imaging contrast than the rest of the head 1102. This shows the user where the divot 1104 is located within the image.

Example 6

Figure 16:
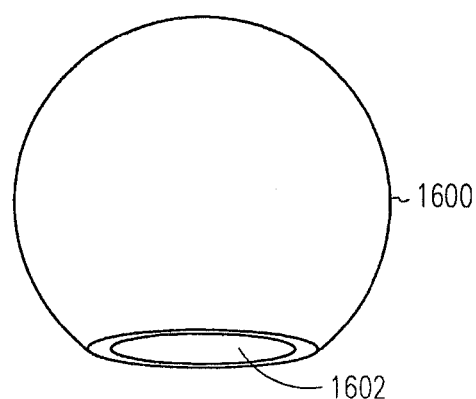
FIG. 16 is a perspective view of an optional fluid absorbing cover (or coating).

FIG. 16 is a perspective view of an optional hydrophilic or hygroscopic foam or other magnetic resonance (MR) imageable cover 1600 for slipping over the substantially spherical head 1102. In this example, the fluid/gel-carrying, fluid/gel-absorbing, or other fluid/gel-incorporating cover includes a circular or similar opening 1602 permitting the shaft 1106 to extend therethrough. In one example, a sterile and biologically safe magnetic resonance (MR) imageable fluid/gel is soaked into the cover 1600 either before or after it is slipped over the head 1102. This allows the head 1102 to be imaged by MR as well as CT. In an alternative example, such multi-modality of imaging is similarly implemented using a preformed MR-imageable or other coating upon the head 1102, thereby avoiding any need for slipping a separate cover 1600 over the head 1102. Such a fluid/gel-carrying, fluid/gel-absorbing, fluid/gel-incorporating, or other MR-imageable or other coating could be formed on the external spherical portion of the head 1102, or could additionally be formed in the divot 1104 as well. Examples of suitable coatings capable of soaking up an MR-imageable fluid or gel include, by way of example, but not by way of limitation: foam, silicone, etc. Examples of MR imageable fluids for soaking into the cover 1600 (or coating) include, by way of example, but not by way of limitation: sterile saline, sterile saline or another fluid or gel mixed with gadolinium or another MR-imaging enhancing substance, etc.

Example 7

Figure 17:
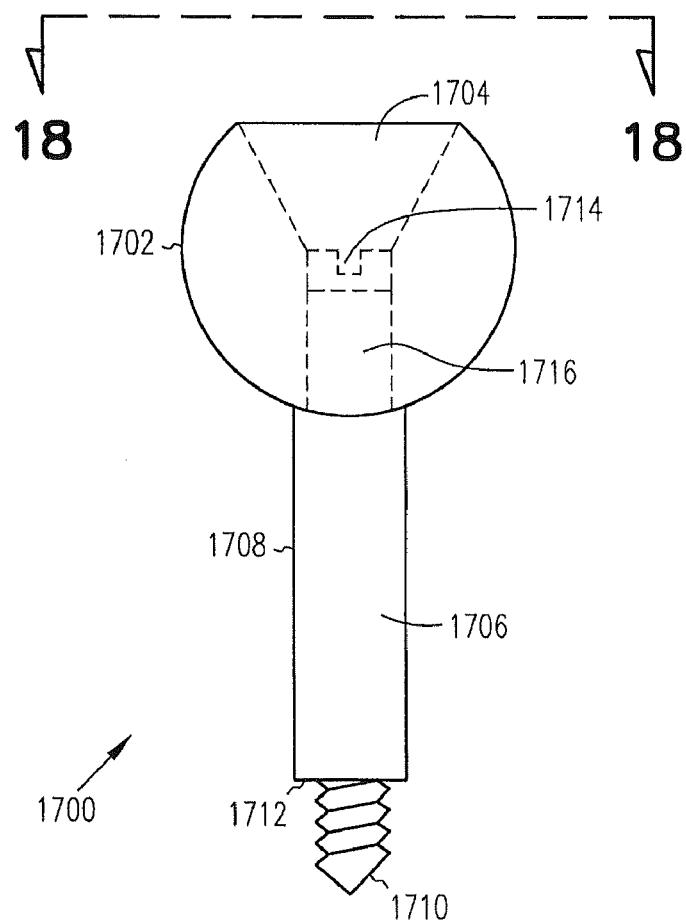
FIG. 17 is a side cross-sectional view of an alternative example of a fiducial marker.
Figure 18:
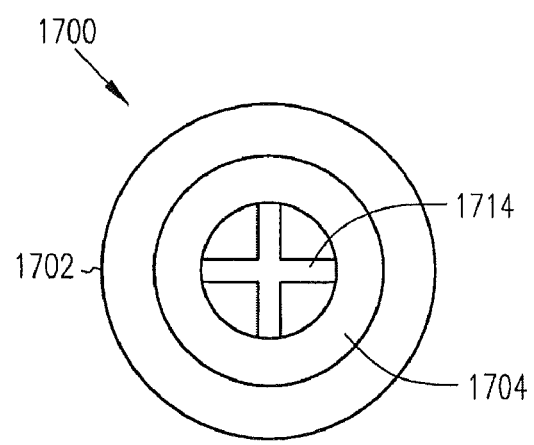
FIG. 18 is a top view of an the fiducial marker of FIG. 17.

FIGS. 17-18 are side cross-sectional and top views, respectively, of an alternative example of a fiducial marker 1700 that is similar in certain respects to the example of FIG. 13. In FIGS. 17-18, the fiducial marker 1700 includes a substantially spherical head 1702. The head 1702 includes a conical or other divot 1704 at its proximal side, and a shaft 1706 extending outwardly from its distal side. In this example, the shaft 1706 includes a proximal portion 1708 and a threaded distal tip portion 1710. The proximal portion 1708 and the threaded distal tip portion 1710 are separated by a shoulder or other seat 1712, such as described above. In this example, the divot 1704 of the head 1702 includes rotational engagement features, such as slots 1714, for receiving a Phillips and/or flathead screwdriver or other driver. Alternatively, an Allen-type receptacle, or any other rotational engagement feature could be used for receiving another driver.

In the example of FIGS. 17-18, the head 1702 is made of a different material than the shaft 1706. In one example, the different materials are selected to provide different image contrasts on a particular imaging modality (e.g., an MR image, a CT image, or even both types of images). In one such example, the head 1702 is relatively more highly visible on the particular imaging modality, and the shaft 1706 is less highly visible on the particular imaging modality.

In one example, this is effected by using a titanium shaft 1706 that includes a proximally projecting post 1716. In one example, a proximal end of the post 1716 provides the slots 1714, as illustrated in FIG. 17. In another example, the slots are instead incorporated into the head 1702. In this example, the head 1702 is a plastic sphere-like object that is insert-molded or otherwise formed about the post 1716. In one example, the external surface of the post 1716 is knurled or roughened to promote adhesion of the head 1702 to the post 1716, such as during the insert-molding process. In one example, the head 1702 is highly MR-visible, while the shaft 1706 is not so highly MR-visible, but instead is radiolucent. In addition to insert-molding, other techniques for affixing the head 1702 to the shaft 1706 include, without limitation, gluing, casting, spin-welding, and ultrasonic welding. In yet another example, the post 1716 is threaded, and the head 1702 is threaded and glued onto the post 1716.

Example 8

Figure 19:
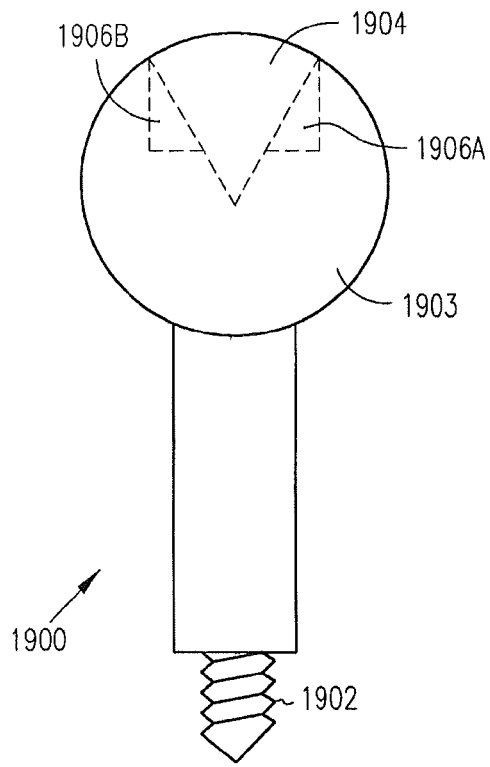
FIG. 19 illustrates a side view of a fiducial marker that includes a self-drilling and self-tapping threaded distal tip portion.

FIGS. 19-23 illustrate various distal tip configurations and techniques of attaching fiducial markers to bone. FIG. 19 illustrates a side view of a fiducial marker 1900 that includes a self-drilling and self-tapping threaded distal tip portion 1902. This example may additionally include a vertical flute-like cutout, as discussed above, for enhancing its self-drilling capability. The head 1903 of the fiducial marker 1902 includes a conical or other divot 1904 and associated slots 1906 or other rotational engagement features for driving the fiducial marker 1900 into bone.

Figure 20:
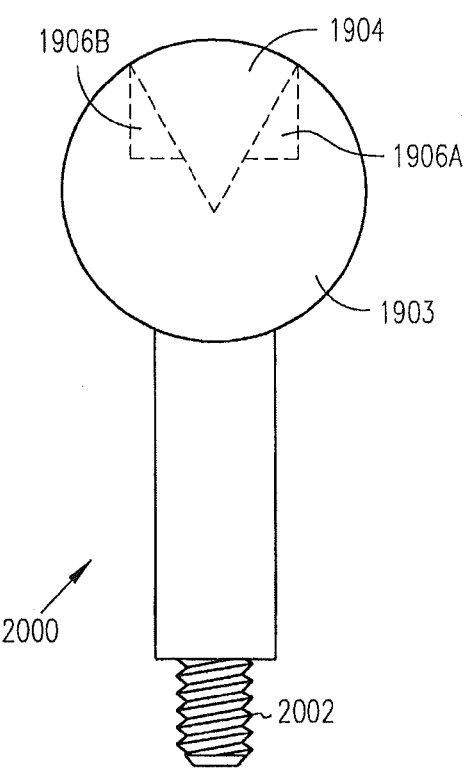
FIG. 20 illustrates a side view of a fiducial marker that includes a threaded distal tip portion that need not be self-tapping and/or self-drilling.

FIG. 20 illustrates a side view of a fiducial marker 2000 that includes a threaded distal tip portion 2002 that need not be self-tapping and/or self-drilling, such as for use when a hole as been pre-drilled into bone for receiving the tip portion 2002. In one such example, the distal tip portion 2002 is neither self-tapping, nor self-drilling. In another such example, the distal tip portion 2002 is self-tapping, but is not self-drilling.

Figure 21:
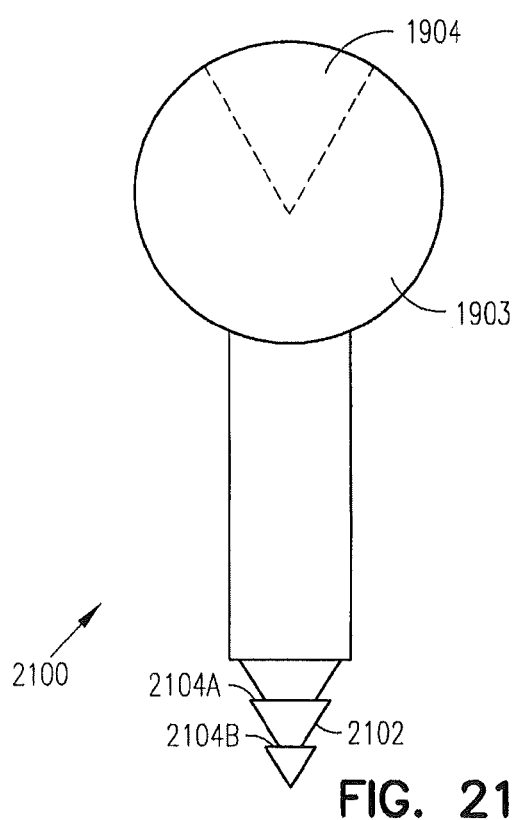
FIG. 21 illustrates a side view of a fiducial marker that includes a barbed distal tip portion.

FIG. 21 illustrates a side view of a fiducial marker 2100 that includes a barbed or other distal tip portion 2102 enabling the fiducial marker 2100 to be driven into bone like a nail or a staple—that is, without needing any rotation. In one example, barbs 2104 help retain the distal tip portion 2102 within the bone. In another example, a nail-like distal tip portion 2102 is used instead. The nail-like distal tip portion 2102 may include a faceted point. In another example, the nail-like distal tip portion 2102 includes anti-rotation features that do not substantially inhibit the distal tip portion 2102 from being driven into bone, but which inhibit rotation after the distal tip portion 2102 has been driven into bone. The fiducial marker 2100 may be removed by grasping and pulling the proximal head 1903, such as with a staple-puller-like tool. Therefore, this example need not include the slots 1906 or other rotational engagement features because rotation is not needed for inserting or removing the fiducial marker 2100.

Figure 22:
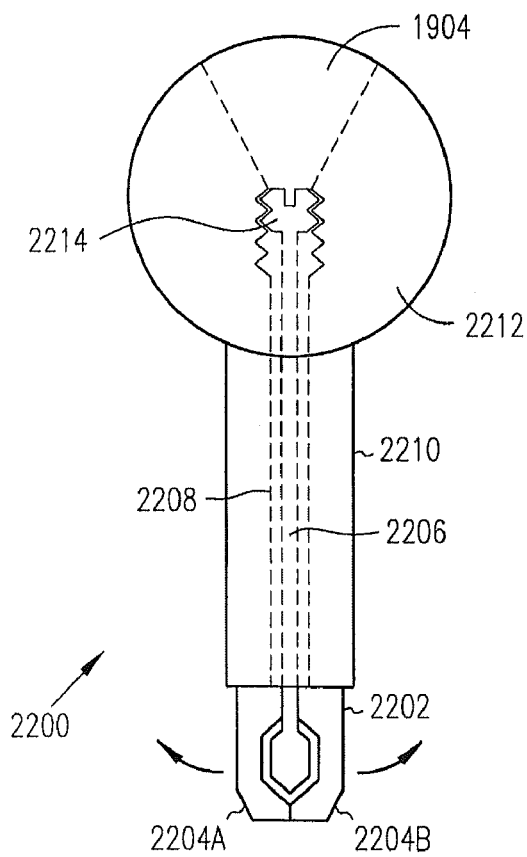
FIG. 22 illustrates a side view of a fiducial marker having a distal tip portion that includes tangs, or another laterally expandable retention element.

FIG. 22 illustrates a side view of a fiducial marker 2200 having a distal tip portion 2202 that includes tangs 2204A-B, or another laterally expandable retention element. In one example, the tangs 2204A-B are pushed outward by an ascending and/or descending longitudinally extending internal rod 2206 that pushes upward or downward against tapered internal shoulders of each of the tangs 2204A-B. This, in turn, pushes the tangs 2204A-B laterally outward in opposite directions. The rod 2206 extends longitudinally through an interior passage 2208 of a shaft 2210. The shaft 2210 extends between the distal tip 2202 and a head 2212 portion of the fiducial marker 2200. In one example, the rod 2206 terminates at a proximal externally threaded drive head 2214 that engages an internally threaded portion of the head 2212. The drive head 2214 includes screwdriver slots or one or more other rotational engagement features for turning the drive head 2214. In one example, turning the drive head 2214 in a clockwise direction moves the drive head 2214 closer to the distal tip 2202 of the fiducial marker 2200. This pushes the rod 2206 downward, which, in turn, pushes the tangs 2204A-B outward to grip bone surrounding a pre-drilled hole into which the distal tip 2202 has been inserted. In another example, turning the drive head 2214 in a counter-clockwise direction moves the drive head 2214 away from the distal tip 2202 of the fiducial marker 2200. This pulls the rod 2206 upward, which, in turn, pushes the tangs 2204A-B outward to grip bone surrounding a pre-drilled hole into which the distal tip 2202 has been inserted.

Figure 23:
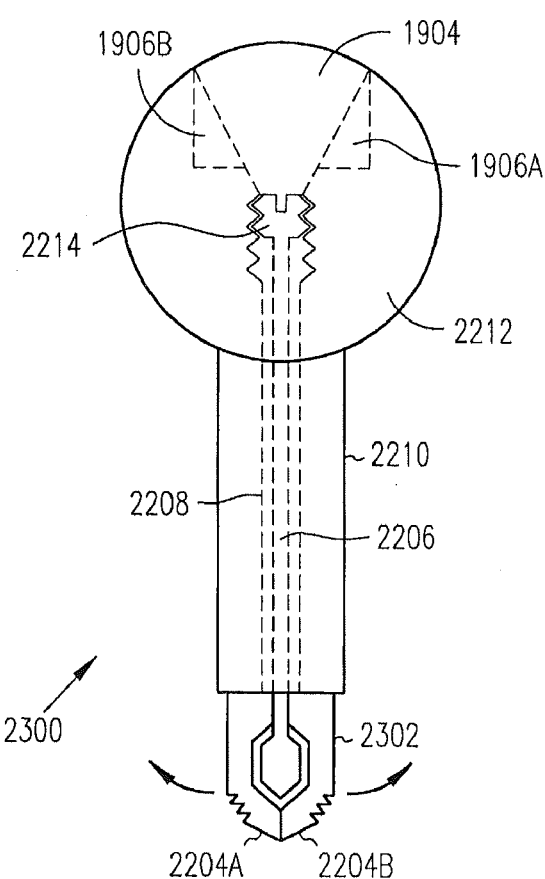
FIG. 23 illustrates a side view of a fiducial marker including a laterally expandable retention element and also having a self-tapping and/or self-drilling externally threaded distal tip portion.

FIG. 23 illustrates a side view of a fiducial marker 2300, similar to the fiducial marker 2200 of FIG. 22, but having a self-tapping and/or self-drilling externally threaded distal tip portion 2302, such as for being introduced into bone without using a pre-drilled hole. The head 2212 of the fiducial marker 2300 of FIG. 23 also includes slots 1906 or other rotational engagement features for rotationally driving the fiducial marker 2300 into bone, such as by using a screwdriver. Then, the tangs 2204A-B are forced outward as described above with respect to the fiducial marker 2200 of FIG. 22.

Example 9

After a fiducial marker has been introduced into a patient's skull or other bone, it may be desirable to protect the fiducial marker, such as against accidental shocks or impacts, "twiddling" by the patient, etc.

Figure 24:
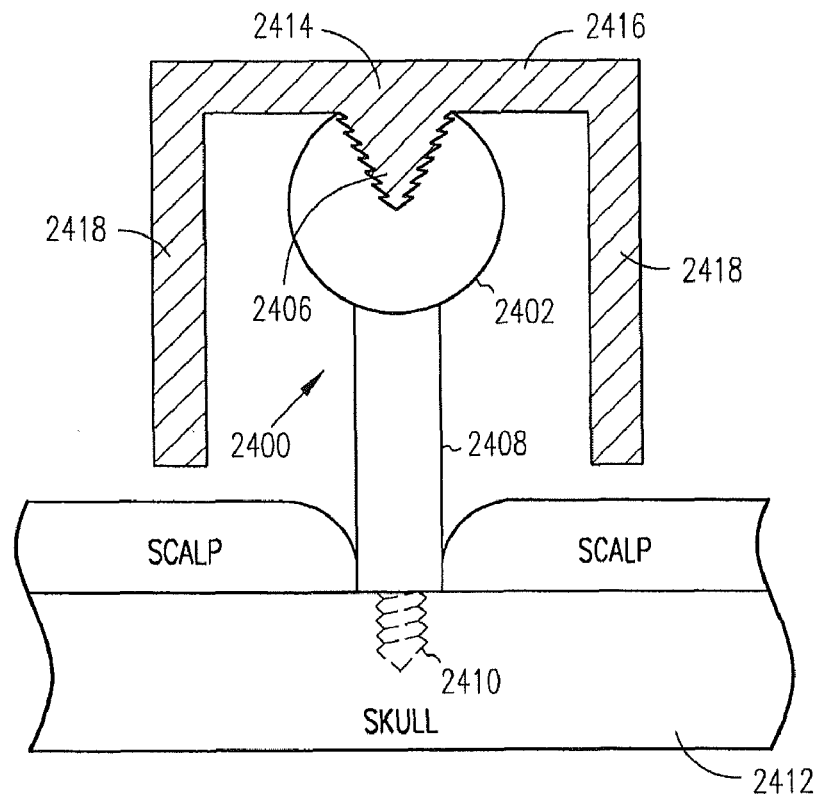
FIG. 24 is a side cross-sectional view of a fiducial marker having a protective cap.

FIG. 24 is a side cross-sectional view of a fiducial marker 2400 having a substantially spherical head 2402 that includes an internally threaded proximal divot 2406, and a shaft 2408 extending outward from a distal side of the head 2402 toward a distal tip 2410 that has been threaded into a portion of the subject's skull 2412. In this example, a protective cap 2414 has been threaded into the divot 2406. The protective cap 2414 includes a disk-like top portion 2416 and a cylindrical circumferential skirt 2418.

Figure 25:
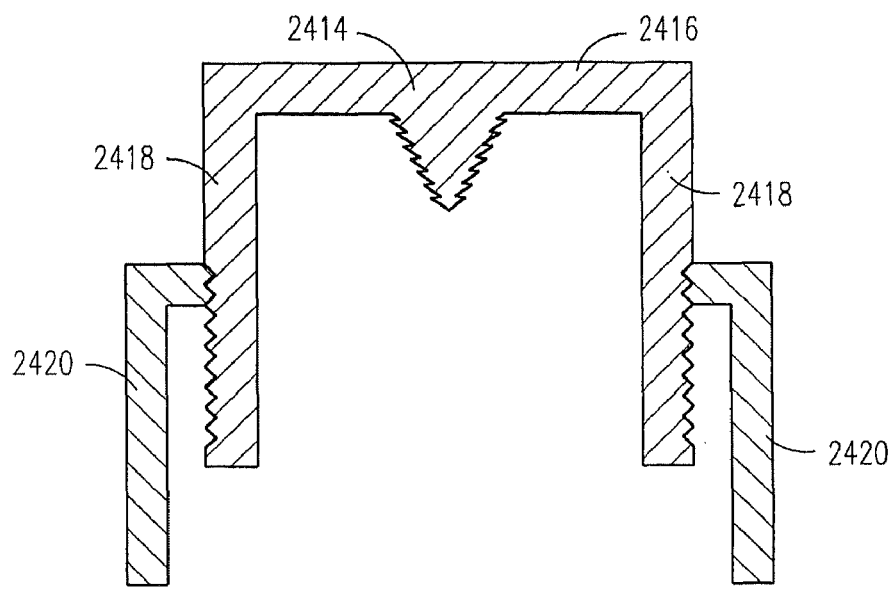
FIG. 25 is a side cross-sectional view of a protective cap with an adjustable-height skirt.

FIG. 25 is a side cross-sectional view of a further example of the protective cap 2414 in which the skirt 2418 includes an adjustable height outer cylindrical circumferential skirt 2420. In this further example, threads on the internal portion of the skirt 2418 engage threads on the outer portion of the skirt 2420, providing height adjustability to accommodate different scalp thicknesses. In use, the fiducial marker 2400 is first affixed to the subject's skull, then the protective cap is threaded into the divot 2406, and then the outer skirt 2420 is lowered to the appropriate height for the particular patient's scalp thickness.

Figure 26:
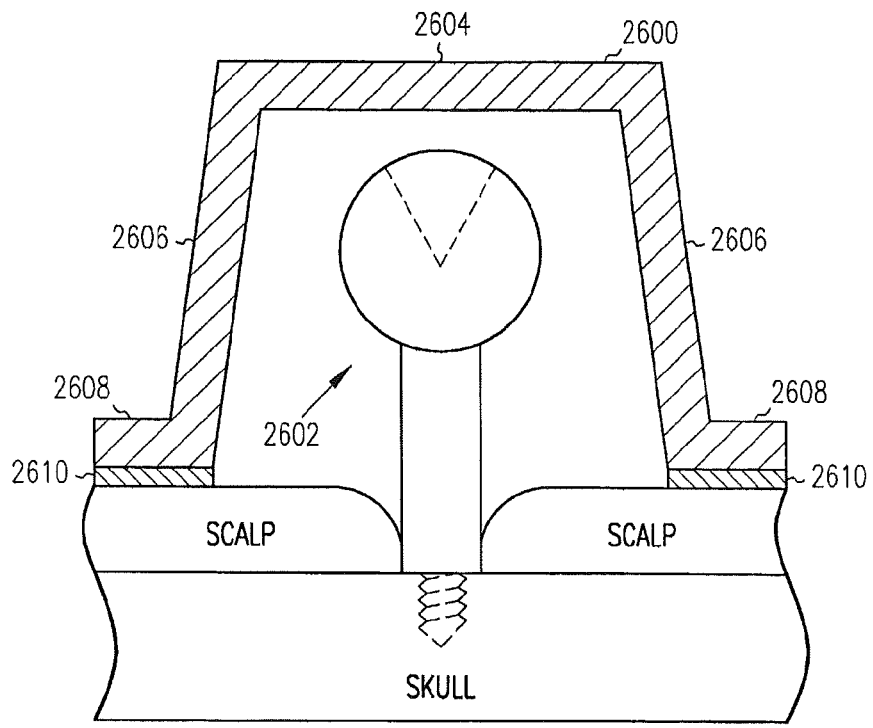
FIG. 26 is a side cross-sectional view of a protective cap disposed about a fiducial marker.

FIG. 26 is a side cross-sectional view of another example of a protective cap 2600, which is disposed about a fiducial marker 2602 that has been affixed to a subject's skull. In this example, the cap 2600 includes a proximal disk portion 2604, a cylindrical circumferential portion 2606, and a distal base ring flange portion 2608. The distal base ring flange portion 2608 includes a self-adhesive coating 2610 on its distal side. This allows attachment of the protective cap 2600 to the patient's scalp.

Figure 27:
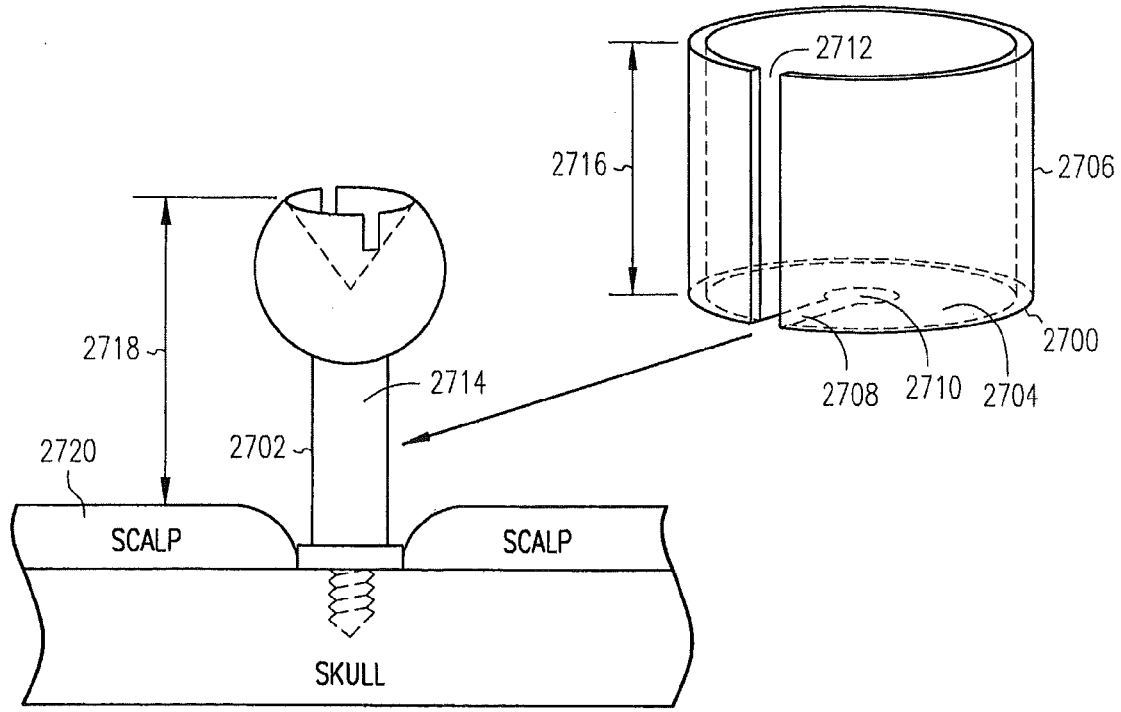
FIG. 27 is a perspective view of a protective collar that can be disposed about a fiducial marker that has been affixed to a subject's skull.

FIG. 27 is a perspective view of a protective collar 2700 that can be disposed about a fiducial marker 2702 that has been affixed to a subject's skull. In this example, the protective collar 2700 includes a disk-like base 2704 and a circumferential cylindrical sidewall 2706 rising upward from a perimeter of the base 2704. The collar 2700 includes a radial slot 2708 in the base 2704. A first end of the radial slot 2708 terminates at an orifice 2710 at the center of the base 2704. A second end of the radial slot 2708 terminates at a peripheral slot 2712, at substantially a right angle thereto, extending up the sidewall 2706 of the collar 2700. The collar 2700 is somewhat flexible (e.g., made of plastic), and the peripheral slot 2712 and the radial slot 2708 are sized and shaped to pass the shaft 2714 of the fiducial marker 2702 through to the center orifice 2710, where it is seated. When the shaft 2714 is seated within the center orifice 2710, a height 2716 of the sidewall 2706 of the collar 2700 is greater than a height 2718 between a top of the fiducial marker 2702 and the patient's scalp 2720. When the collar 2700 has been disposed about the fiducial marker 2702, it protects the fiducial marker 2702 against a mechanical impact.

Figure 28:
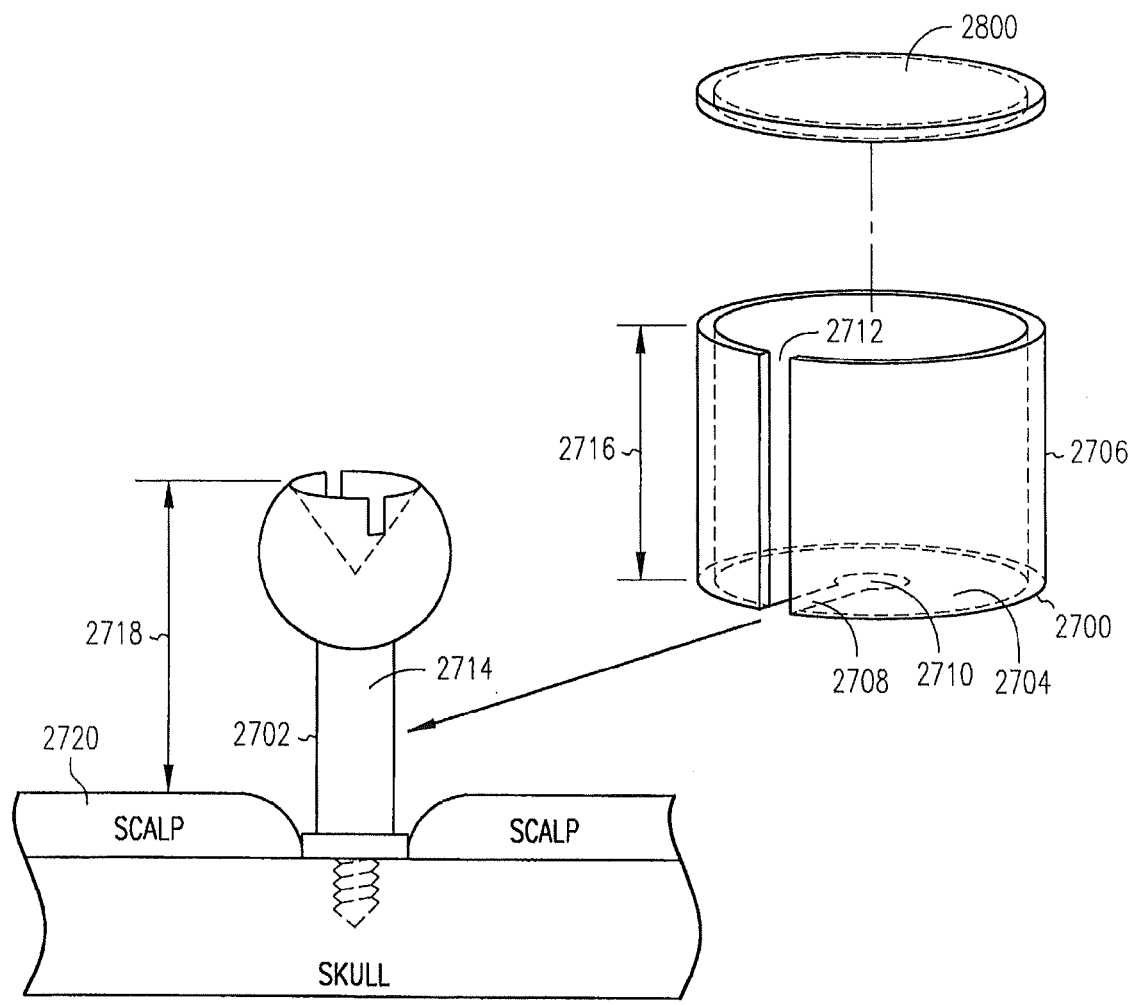
FIG. 28 is a perspective view of a protective collar and cap.

FIG. 28 is a perspective view of the collar 2700 further including a disk-like cap 2800 that fits snugly over and around the top of the collar 2700 to house and substantially enclose the fiducial marker 2702 disposed within the collar 2700. The cap 2800 is not required, but it provides additional structural strength and helps keep clean the incision through which the fiducial marker 2702 was introduced.

Figure 29:
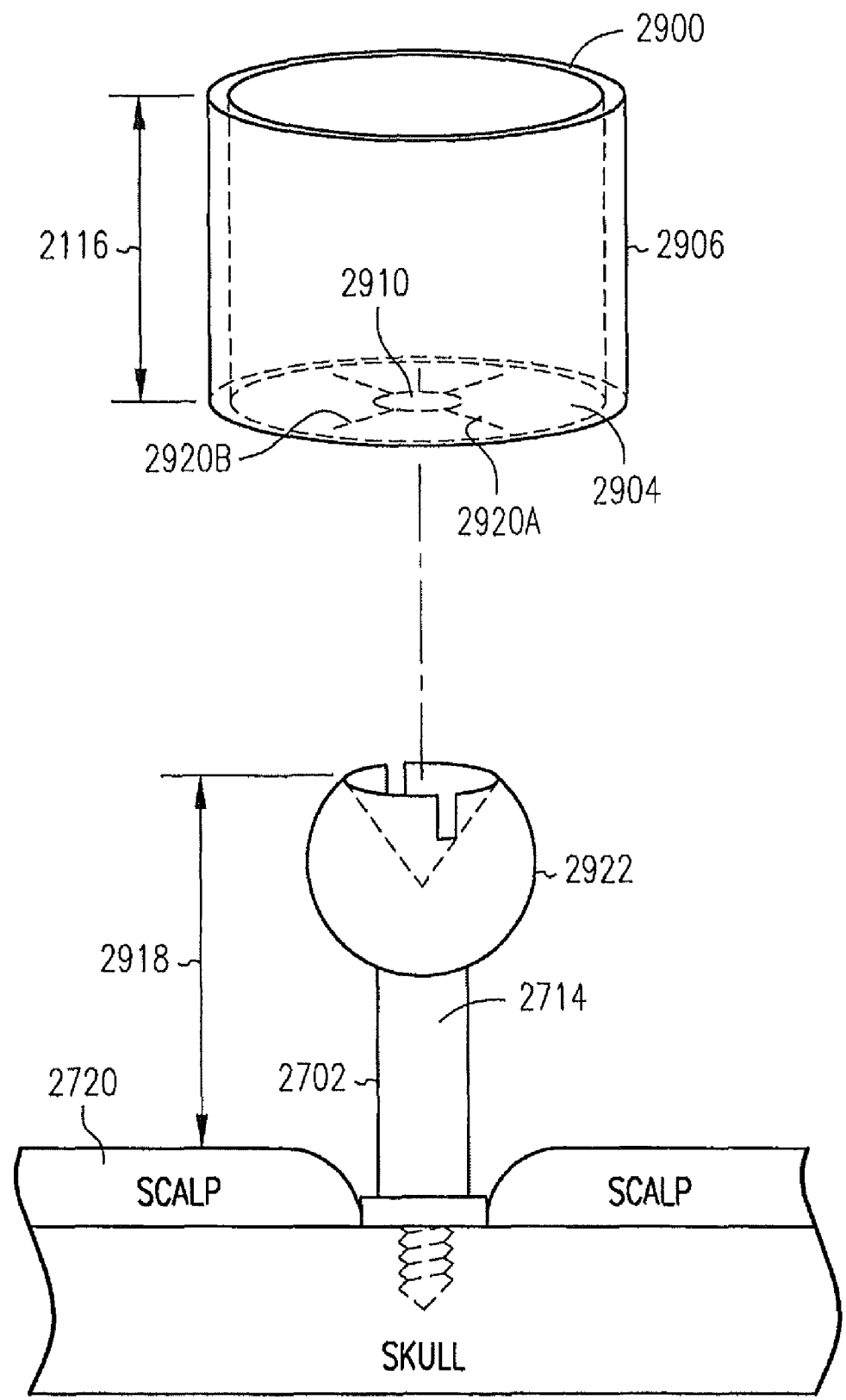
FIG. 29 is a perspective view of an alternate example of a protective collar that can be slipped over a fiducial marker.

FIG. 29 is a perspective view of an alternate example of a collar 2900, similar to that illustrated in FIGS. 27-28, but that omits the radial slot 2708 and the peripheral slot 2712. In this example, the protective collar 2900 includes a disk-like base 2904 and a circumferential cylindrical sidewall 2906 rising upward from a perimeter of the base 2904. The collar 2900 includes an orifice 2910 at the center of the base 2904. The flexible base 2904 includes small incisions 2920 extending radially from the orifice 2910 to permit the head 2922 portion of the fiducial marker 2702 (which is larger than the orifice 2910) to pass through the orifice 2910. The orifice 2910 is sized to accommodate the shaft 2714 portion of the fiducial marker 2702 snugly therein. When the collar 2900 is seated against the scalp 2720, a height 2916 of the sidewall 2906 of the collar 2900 is greater than a height 2918 between a top of the fiducial marker 2702 and the scalp 2720 of the patient. When the collar 2900 has been disposed about the fiducial marker 2702, it protects the fiducial marker 2702 against a mechanical impact, etc. The collar 2900 can also be used in conjunction with the cap 2800 illustrated in FIG. 28, as discussed above.

Figure 30:
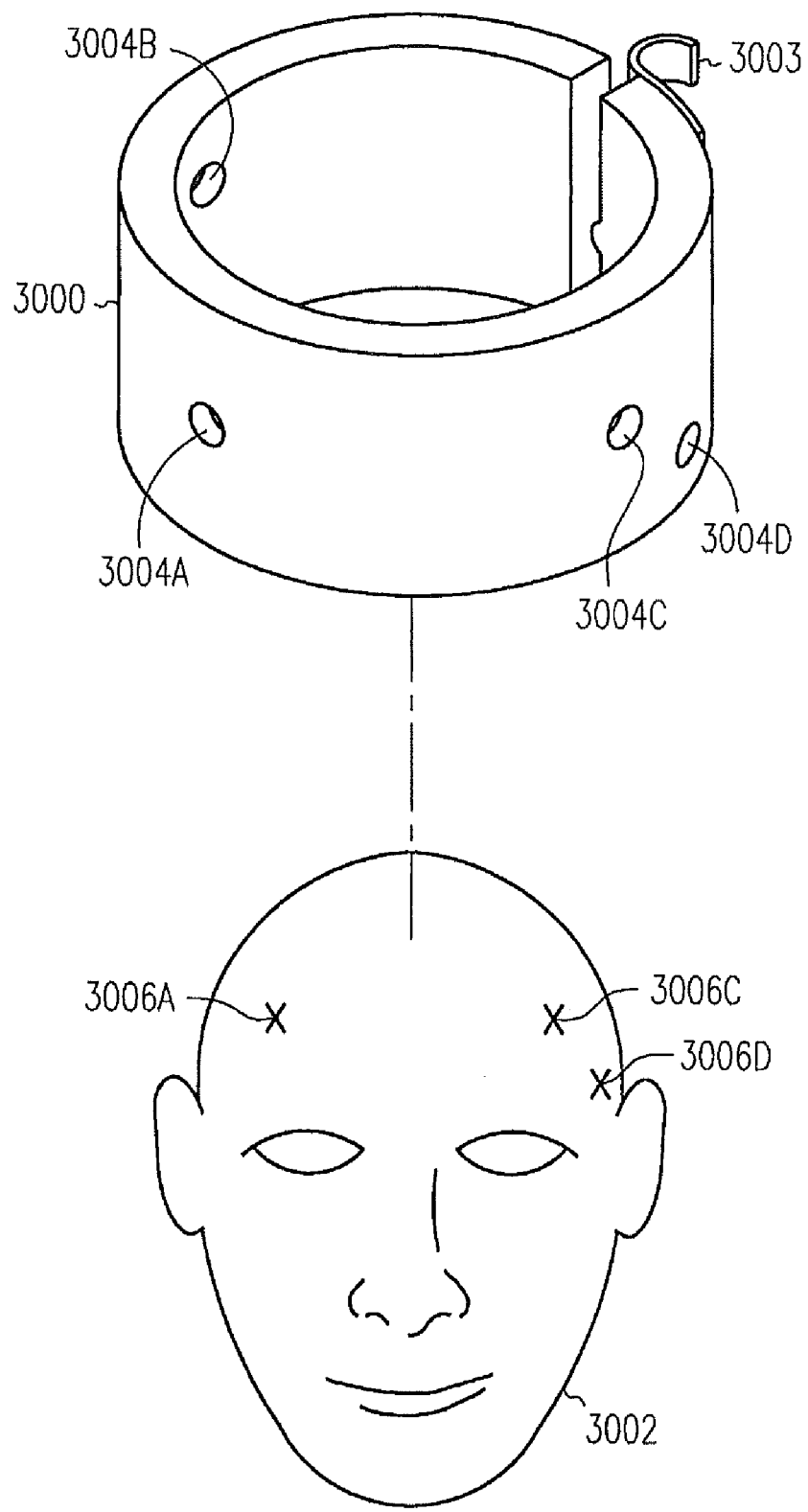
FIG. 30 is a perspective view illustrating an example of a headband for protecting fiducial markers from mechanical impact.

FIG. 30 is a perspective view illustrating an example of a headband 3000 for protecting fiducial markers from mechanical impact. The headband 3000 is sized and shaped to fit around the skull of a subject 3002. The headband includes one or more fixation straps 3003, e.g., using Velcro to attach opposing sides of the headband 3000. In one example, the headband 3000 includes one or more pre-formed holes 3004, which are located in relationship to each other in a manner to be suitable for placing image-guided surgical (IGS) fiducial markers at the locations 3006 of the holes when the headband 3000 is placed about the subject's head. In an alternative example, the headband 3000 does not include such holes 3004. Instead, the user cuts holes in the headband 3000 as desired for locating the fiducial markers. In yet another example, the holes 3004 are replaced by perforation openings, so that the underlying fiducial marker only pokes through the headband as much as is needed.

Figure 31:
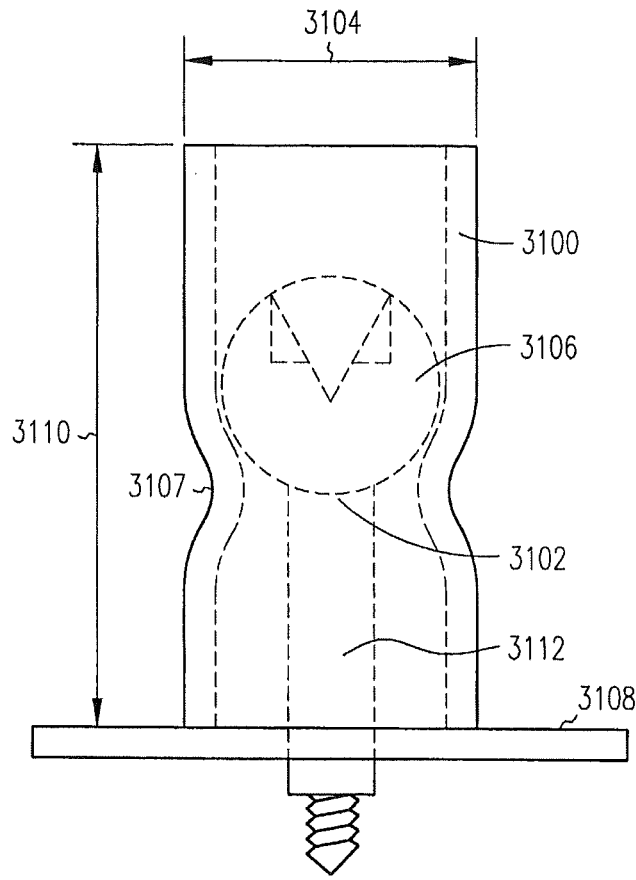
FIG. 31 is a side view illustrating an example of a tubular protective guide collar.

FIG. 31 is a side view illustrating an example of a tubular protective guide collar 3100. The guide collar 3100 carries a fiducial marker 3102. The guide collar 3100 is useful for holding and guiding the fiducial marker 3102 while it is being affixed to the patient's skull, as well as for protecting the fiducial marker 3102 after it has been affixed to the patient's skull. In this example, the tubular guide collar 3100 includes an inner diameter 3104 that is large enough to receive the head 3106 of the fiducial marker 3102. An intermediate portion of the guide collar 3100 includes a circumferential neck 3107. The neck 3107 has a slightly smaller inner diameter than the diameter of the head 3106. However, the neck 3107 is flexible, deformable, and/or compliant enough to pass the head 3106 through the neck 3107 when the fiducial marker 3102 is affixed to the patient's skull—without pulling the fiducial marker 3102 loose from the patient's skull. This can be accomplished by constructing the guide collar 3100 of a somewhat compliant plastic, and providing appropriate neck dimensions for a particular fiducial marker head 3106. The guide collar 3100 also optionally includes a distal flange 3108, such as to provide additional stability and to enhance vertical orientation of the guide collar 3100. The user can hold the guide collar 3100 in place, such as by pressing two fingers against the flange 3108 to hold it against the patient's scalp. This properly holds straight and orients the fiducial marker 3102 as it is threaded into or otherwise affixed to the subject's skull. It promotes an orthogonal orientation of the fiducial marker 3102 with respect to the subject's skull.

Figure 32:
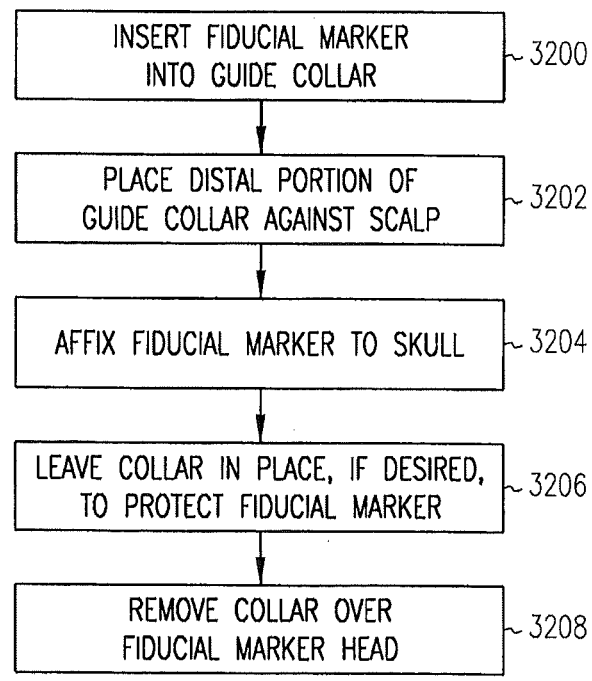
FIG. 32 is a flow chart illustrating one example of using a guide collar.

FIG. 32 is a flow chart illustrating one example of using the guide collar 3100. At 3200, the fiducial marker 3102 is dropped into a proximal end of the guide collar 3100. The fiducial marker 3102 falls through the proximal tubular portion and comes to rest against the interior portion of the neck 3106, as illustrated in FIG. 31. Then, at 3202, a distal end of the guide collar 3100 is positioned against the subject's scalp, such as by pressing down against the optional flange 3108. At 3204, the fiducial marker 3102 is affixed to the subject's skull, such as by inserting a screwdriver tip into the proximal end of the guide collar 3100 and into corresponding screwdriver slot(s) in the head 3106 of the fiducial marker 3102, and screwing the fiducial marker 3102 into the patient's skull. At 3206, the guide collar 3100 can be left in place, if desired, to protect the fiducial marker 3102 against a mechanical impact. When the fiducial marker 3102 is affixed to the patient's skull, and the flange 3108 rests against the patient's scalp, the height 3110 of the guide collar 3100 is greater than the corresponding height of the fiducial marker 3102, such that the fiducial marker head 3106 is still located within the tubular guide collar 3100. This protects the fiducial marker 3100, such as from an axial mechanical impact that otherwise might potentially drive the fiducial marker 3100 deeper into the patient's skull. At 3208, the guide collar 3100 can be removed while leaving the fiducial marker 3102 affixed to the subject's skull. This can be accomplished by grasping and pulling on the guide collar 3100, or by prying under the flange 3108. As discussed above, the neck 3107 is sufficiently compliant to pass the head 3106 from the proximal portion of the hourglass-shaped guide collar 3100 to its distal portion. This allows the guide collar 3100 to be removed over the top of the fiducial marker 3102 while leaving it in place. Alternatively, the fiducial marker 3102 could be affixed to the subject without using the guide collar 3100, and the guide collar 3100 could later be snapped into place over the fiducial marker 3102 to protect it against a mechanical impact, as discussed above.

Figure 33:
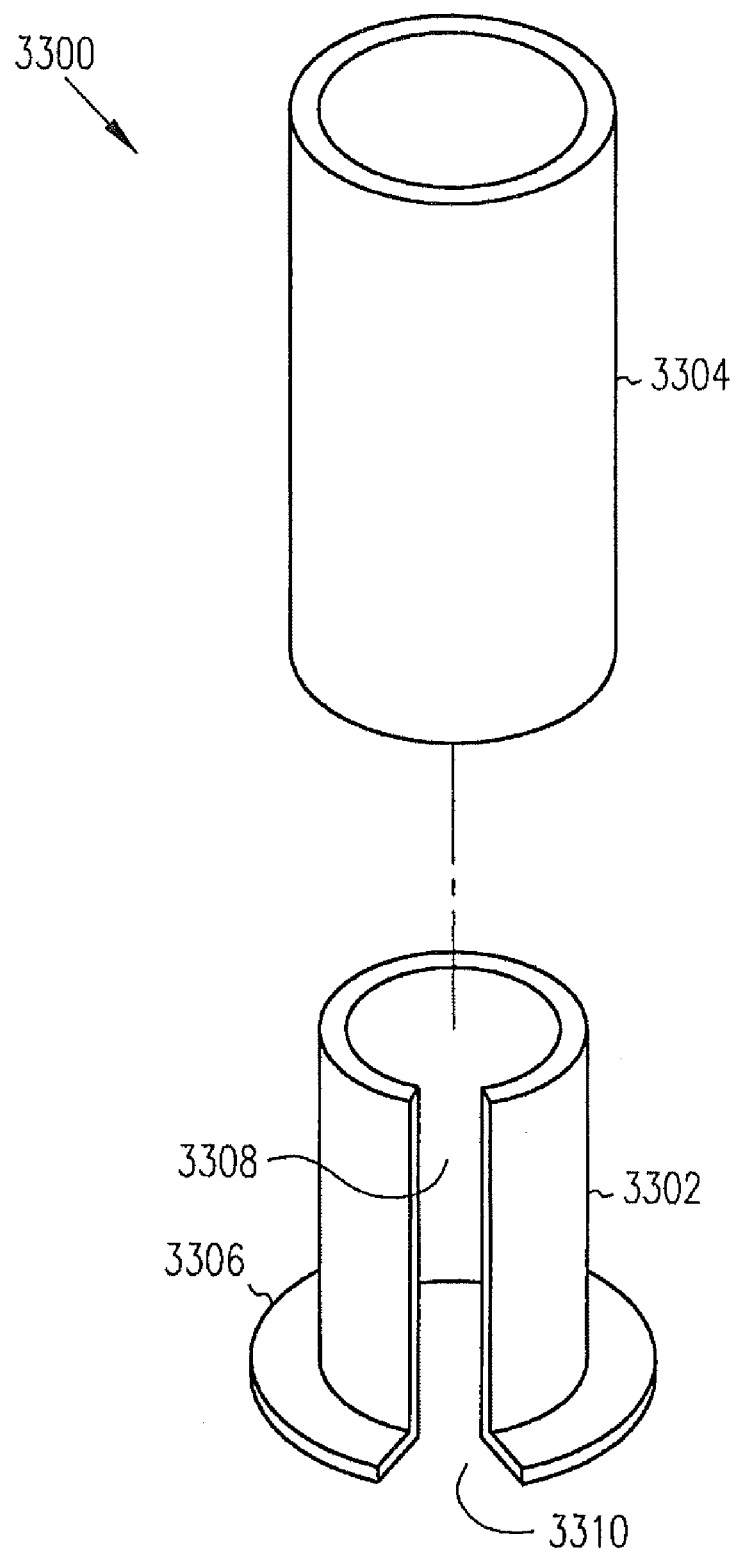
FIG. 33 is a perspective view of an alternative guide collar.

FIG. 33 is a perspective view of an alternative guide collar 3300. In this example, the guide collar 3300 has more than one piece. In FIG. 33, the guide collar 3300 includes a cylindrical tubular guide base 3302 and a cylindrical height extender 3304. In this example, the cylindrical tubular guide base 3302 includes an optional distal flange 3306. The guide base 3302 includes a side access slot 3308 that is sized and shaped to pass a shaft portion 3112 of the fiducial marker 3102. The flange 3310 includes a similar slot 3310, which is aligned with the slot 3308. The cylindrical height extender 3303 can be press-fit over the guide base 3302 snugly enough to hold these two pieces together until they are again pulled apart by the user.

Figure 34:
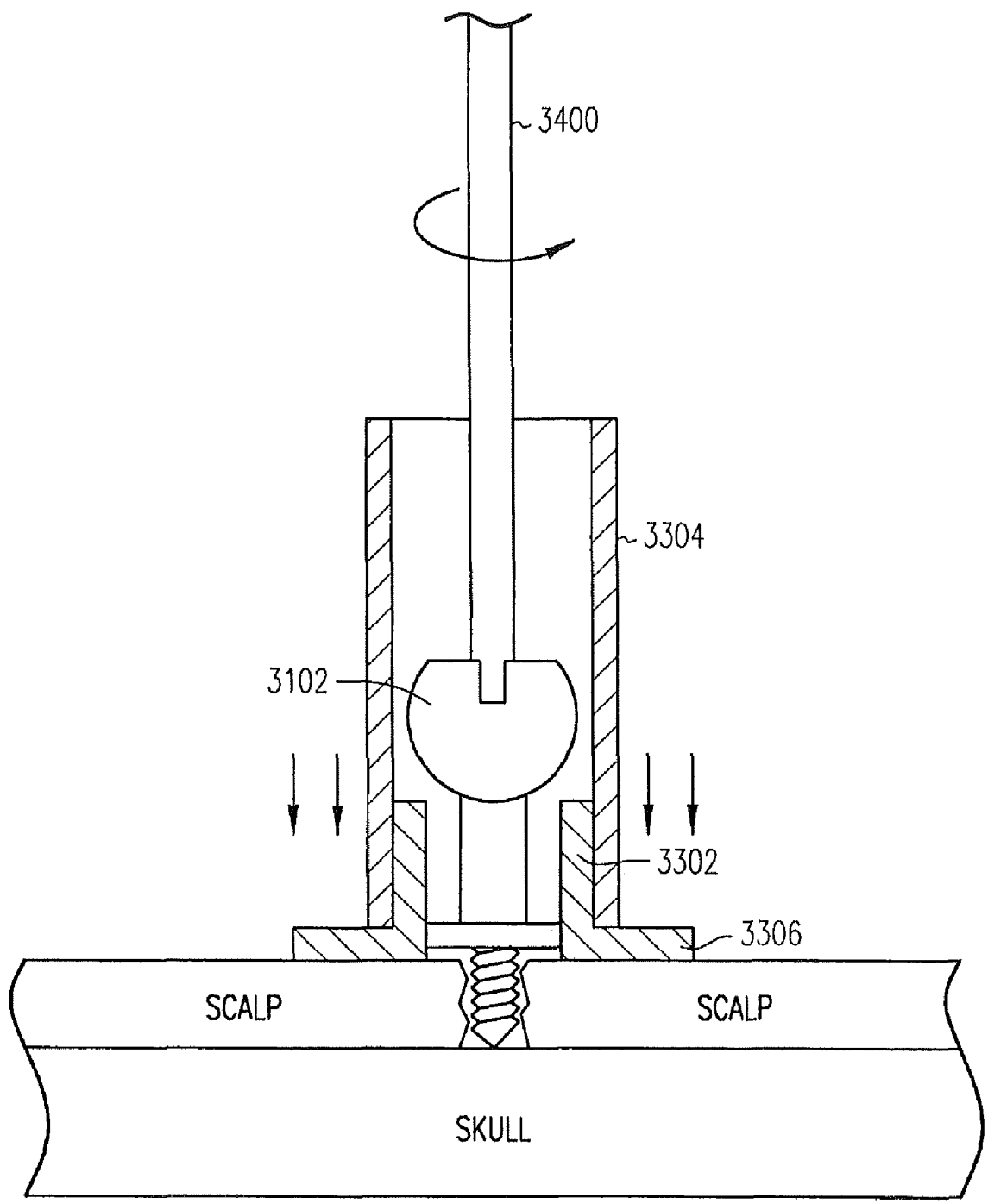
FIG. 34 is a side sectional view of a guide base, a height extender, a fiducial marker, and a screwdriver shaft.
Figure 35:
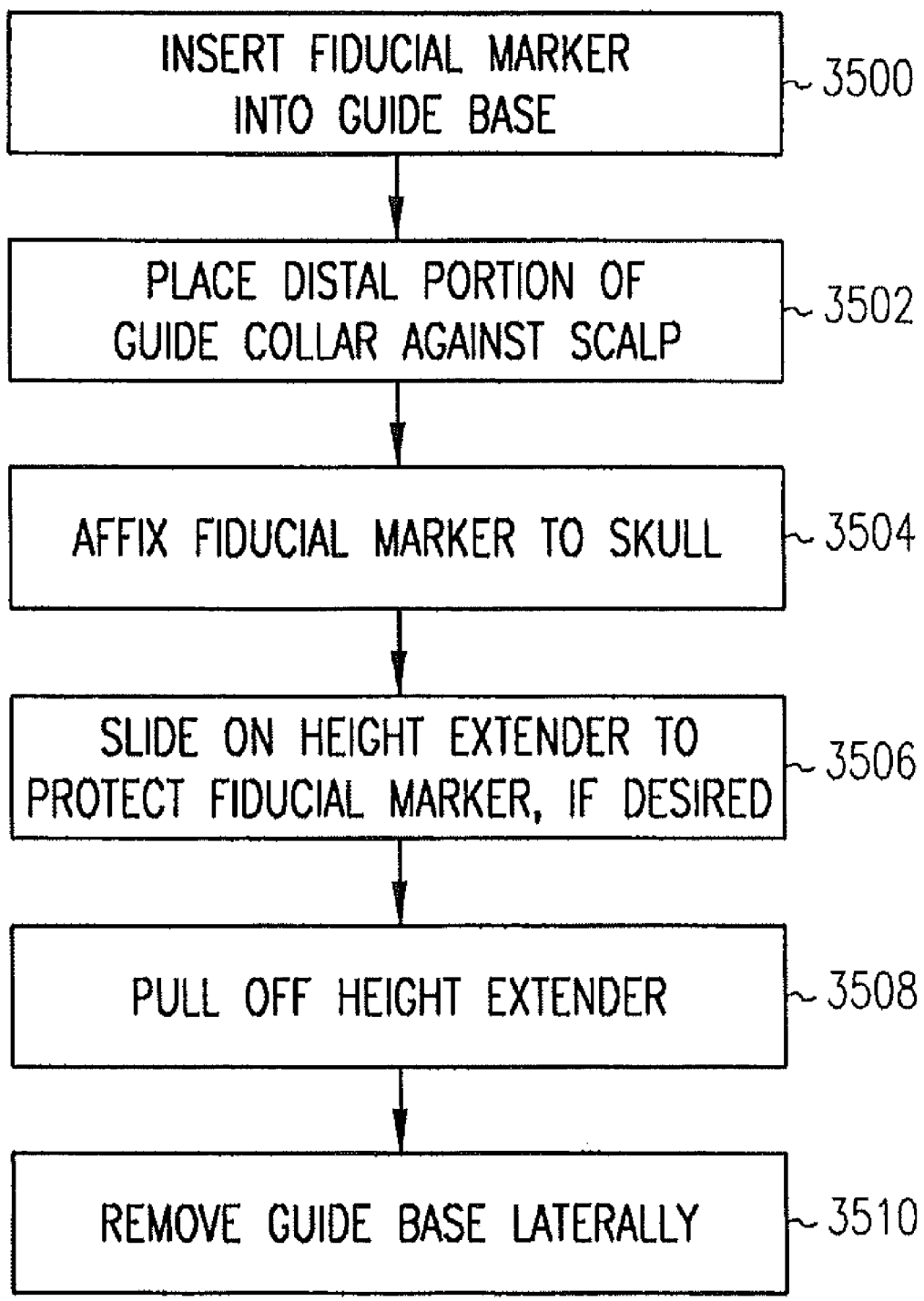
FIG. 35 is a flow chart illustrating one example of using a guide base and a height extender.

FIG. 34 is a side sectional view of the guide base 3302, the height extender 3304, a fiducial marker 3102, and a screwdriver shaft 3400. FIG. 35 is a flow chart illustrating one example of using the guide base 3302 and the height extender 3304 of FIGS. 33-34. At 3500, the fiducial marker 3102 is inserted into the guide base 3302, either by dropping it in the top or by inserting its shaft laterally through the side access slot 3308. At 3502, a distal portion of the guide base 3302 is placed against the subject's scalp and held in place, such as by pressing down against the optional flange 3306. At 3504, the fiducial marker 3102 is affixed to the subject's skull, such as by screwing it in such as illustrated in FIG. 34. At 3506, the height extender 3304 is slid over and snugly press-fitted around the guide base 3302. As illustrated in FIG. 34, the height extender 3304 is taller than the affixed fiducial marker 3102. In this manner, the height extender 3304 protects the fiducial marker 3102 against a mechanical impact, such as an axial blow that might otherwise drive the fiducial marker 3102 deeper into the patient's skull. At 3508, the height extender 3304 is removed by axial pulling. At 3510, the guide base 3304 is laterally removed, thereby passing the shaft of the fiducial marker 3102 out of the slot 3308.

Figure 36:
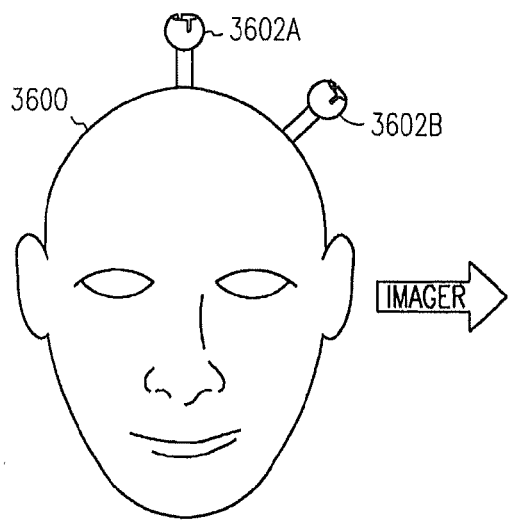
FIG. 36 is a schematic illustration of a subject with one or more fiducial markers affixed to the subject's skull.
Figure 37:
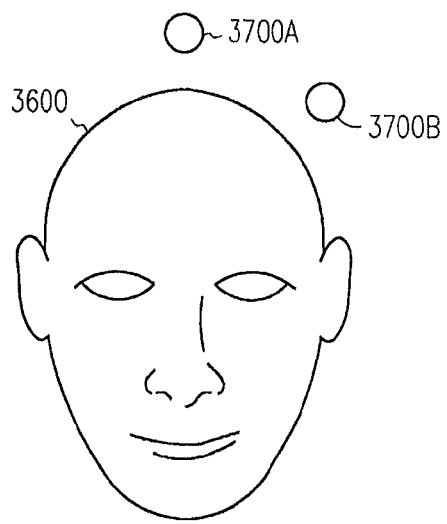
FIG. 37 illustrates schematically one example of how such fiducial marker head images appear on an image.

FIG. 36 is a schematic illustration of a subject 3600 with one or more fiducial markers 3602 affixed to the subject's skull. As discussed above, in one example, the fiducial markers 3602 include substantially spherical heads with integrated conical divot receptacles therein for mating to a remotely detectable positioning instrument. FIG. 37 illustrates schematically one example of how such fiducial marker head images 3700 appear on an image created by MR, CT, or another imaging modality. For registering the patient, it is useful to know the center locations of the fiducial marker head images 3700. However, the presence of the integrated divot may confound the fiducial marker head images 3700 somewhat.

Figure 38:
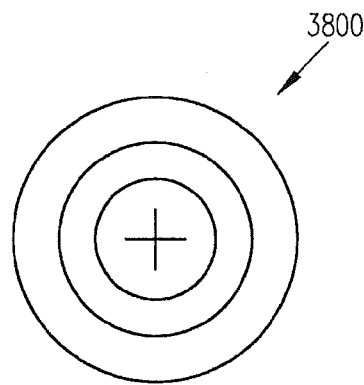
FIG. 38 illustrates schematically one example of a template, such as for assisting a user in locating respective centers of fiducial marker head images.

FIG. 38 illustrates schematically one example of a template 3800 including one or more concentric rings with a center indicator (such as a bull's-eye pattern or the like) such as for assisting the user in locating the center of the fiducial marker head images 3700. In one example, the template 3800 is implemented on a physical media (e.g., a transparency) that is placed over the fiducial marker head image 3700 (e.g., on a computer display, such as the IGS workstation 400). In another example, the template 3800 is implemented by computer software (e.g., as a mouse-draggable icon or feature on a computer display, such as the IGS workstation 400) that is moved using a mouse or other computer input device to place it over a fiducial marker head image 3700. In either example, the template 3800 is concentrically aligned (e.g., using one or more of its concentric rings or similar curves for aligning with a two-dimensional image of a sphere) to one of the fiducial marker head images 3700. This provides an indication of the center of that fiducial marker head image 3700. In the physical media example, the user moves a cursor to align the fiducial marker head image 3700 with the center of the template, and clicks a mouse button to select the center of the fiducial marker head image 3700. In the software template 3800 example, the user clicks a mouse button when the software template 3800 is aligned with a center of the fiducial marker head image 3700 to select the same. The selected center of the fiducial marker head image 3700 is then used, during the patient registration process, to correlate to the physical location of the apex of the conical divot, as located by the tip of the positioning device that mates thereto, as discussed above.

Although the above examples illustrated with respect to FIGS. 11-38 have been discussed with particular emphasis on a spherical imageable fiducial marker with integrated receptacle and bone screw, it should be understood that in an alternative embodiment, such examples are implemented using a cylindrical or faceted columnar shaped fiducial marker with integrated receptacle and bone screw. Moreover, in a further example, such fiducial markers include reflective outer surfaces that are recognizable by a remote positioning system, as discussed elsewhere in this document. Still further, such fiducial markers can incorporate anti-microbial properties, such as by using an anti-microbial coating, or using silver or silver-based alloys for their manufacture.

In further examples, the various above-described locators (e.g., on the subject's skull, or on a wand, as illustrated in FIG. 3) alternatively or additionally include an electromagnetic (EM) coil that permits determination of the position of the locator using an EM coil detecting positioning system coupled to an IGS workstation rather than the optical positioning system 412 discussed above.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A fiducial marker member locatable by an imaging system, comprising:
   a unitary fiducial marker having an imageable fiducial location head and a shaft extending directly outward from the imageable fiducial location head;
   wherein the imageable fiducial location head is substantially spherical and has a receptacle wall that defines a conical receptacle extending from a cut out opening in the imageable fiducial location head to an apex corresponding to a centroid of the imageable fiducial location head,
      wherein the cut out opening is sized and shaped for allowing a locator instrument of a positioning system to enter and engage the apex of the conical receptacle,
      wherein the receptacle wall is substantially straight from the cut out opening to the apex of the conical receptacle,
   wherein at least a portion of the shaft defines a structure operable to be directly secured to a bone,
   wherein the shaft includes a laterally expandable distal tip and defines a passage extending from the receptacle into the shaft; and
   a member configured to expand the laterally expandable distal tip as the member is moved within the passage in the shaft and toward the distal tip.

2. The fiducial marker of claim 1, wherein the imageable fiducial location head further comprises at least one slot formed between two slot walls of the imageable fiducial location head, the at least one slot being sized and shaped to accommodate a blade or tip of a driver for turning and threading the shaft into the bone.

3. The fiducial marker of claim 2, wherein the two slot walls extend from the conical receptacle.

4. The fiducial marker of claim 3, wherein the at least one slot comprises:
at least four slots distributed about a proximal side of the imageable fiducial location head and extending from the conical receptacle in a generally cruciform shape.

5. The fiducial marker of claim 1, wherein the receptacle wall is a substantially continuously sloping wall from the cut out opening having an edge defined by a surface of the fiducial location head to the apex at the centroid.

6. The fiducial marker of claim 1, wherein the imageable fiducial location head includes a hygroscopic material.

7. The fiducial marker of claim 1, further comprising:
a thread having a major diameter formed on the shaft; and
a seat formed by a wall extending at an angle relative to an axis of the shaft, wherein the seat has a larger diameter than the major diameter of the thread and the seat provides a shoulder acting as a depth stop that inhibits the fiducial marker from being further advanced into the bone;
wherein the shaft includes an unthreaded portion separating an externally threaded portion of the shaft from the imageable fiducial location head.

8. The fiducial marker of claim 1, further comprising:
a kerf operable to accommodate therein loose bone fragments that are channeled upward by a thread on the shaft as the shaft is twisted into the bone.

9. The fiducial marker of claim 1, wherein a first material of the imageable fiducial location head provides a different imaging contrast than a second material of the shaft, wherein the first material and the second material are different.

10. The fiducial marker of claim 1, further including an imageable plug that is sized and shaped to fit within the conical receptacle.

11. The fiducial marker of claim 10, wherein the imageable fiducial location head includes a slot and the imageable plug includes a fin;
wherein the slot and the fin are operable to cooperate such that the imageable fiducial location head and the imageable plug together present a uniformly shaped imageable portion to an imaging system.

12. The fiducial marker of claim 1, further including a cover sized and shaped to fit over the imageable fiducial location head.

13. The fiducial marker of claim 1, further comprising a protective collar, having:
a disk-like base having center orifice; and
a circumferential peripheral cylindrical sidewall extending away from the disk-like base and substantially open at a proximal end of the circumferential peripheral cylindrical sidewall away from the disk-like base.

14. The fiducial marker of claim 13, wherein the protective collar further comprises at least one radial slot in the disk-like base extending from the orifice.

15. The fiducial marker of claim 1, further comprising a headband defining holes sized and shaped for protecting the imageable fiducial location head.

16. A fiducial marker locatable by an imaging system, comprising:
a unitary fiducial marker having:
a substantially spherical imageable fiducial locator head defining a conical receptacle that is sized and shaped for receiving a locator instrument of a positioning system, the conical receptacle defined by a receptacle wall extending from a cut out opening in the substantially spherical imageable fiducial locator head to permit access to a centroid of the substantially spherical imageable fiducial locator head and at least one slot extending from the conical receptacle to be engaged by a driving instrument; and
a shaft that extends directly outward from the substantially spherical imageable fiducial locator head, at least a portion of the shaft being configured for being directly secured to a bone when the driving instrument drives the substantially spherical imageable fiducial locator head and shaft together, wherein the shaft includes a laterally expandable distal tip; and
a member extending through a passage defined by at least a portion of the substantially spherical imageable fiducial locator head and at least a portion of the shaft to engage the expandable distal tip, wherein the member is operable to be accessed to manipulate the member to expand the expandable distal tip, wherein the passage has internal threads and the member has external threads, where the internal and external threads cooperate to move the member axially when the member is rotated.

17. The fiducial marker of claim 16, wherein the receptacle wall is a substantially continuously sloping wall from the cut out opening having an edge defined by a surface of the substantially spherical fiducial locator head to an apex at the centroid.

18. The fiducial marker of claim 16, further comprising:
a kerf to accommodate therein loose bone fragments that are channeled upward by a thread on the shaft as the unitary fiducial marker is being secured to the bone.

19. The fiducial marker of claim 16, further including an imageable plug with a fin that is sized and shaped to fit within the conical receptacle;
wherein the at least one slot and the fin are operable to cooperate such that the substantially spherical imageable fiducial locator head and the imageable plug together present a uniformly shaped imageable portion to the imaging system.

20. The fiducial marker of claim 16, further comprising:
a protective collar, having:
a disk-like base having center orifice;
a circumferential peripheral cylindrical sidewall extending away from the disk-like base and substantially open at a proximal end of the circumferential peripheral cylindrical sidewall away from the disk-like base; and
a disk-like cap sized and shaped to fit over a proximal portion of the circumferential peripheral cylindrical sidewall.

21. The fiducial marker of claim 16, further comprising:
a guide collar assembly having a first member disposed within a second member;
wherein the guide collar assembly is operable to guide the unitary fiducial marker during insertion;
wherein the second member is operable to be removed while the first member remains to protect the unitary fiducial marker.

22. A method of positioning and using a fiducial marker comprising:
driving directly into a bone of a patient a unitary fiducial marker device including a substantially spherical imageable fiducial locator head with an inverted conical receptacle having an apex at the center of the substantially spherical imageable fiducial locator head and defined by a substantially straight receptacle wall extending directly from a cut out in a proximal surface to the apex of the inverted conical receptacle in the substantially spherical imageable fiducial locator head, the conical receptacle is sized and shaped to permit access to a center of the substantially spherical imageable fiducial locator head by mating with an instrument detectable by a positioning system;

engaging a member positioned within a shaft that extends from the substantially spherical imageable fiducial locator head through the conical receptacle;

rotating the member to axially move the member and laterally expand the distal portion of the unitary fiducial marker device to assist in affixing the unitary fiducial marker device to the bone;

obtaining an image of the patient including the substantially spherical imageable fiducial locator head;

accessing the apex with the instrument by moving the instrument towards the apex through the cut out in the proximal surface of the substantially spherical imageable fiducial locator head; and mating the instrument to the receptacle to register an actual position of the patient to the image of the patient.

23. The method of claim 22, further comprising:

disposing a guide collar assembly having a first member around the unitary fiducial marker while driving directly into the bone of the patient the unitary fiducial marker device;

passing a second member of the guide collar assembly over the first member of the guide collar assembly while maintaining the unitary fiducial marker device within the first member; and maintaining both the first member and the second member of the guide collar assembly encircling the unitary fiducial marker device during a time period in which the patient is to be protected against a mechanical impact to the unitary fiducial marker device.

24. The method of claim 22, further comprising:

positioning a tubular protective guide collar adjacent a selected location for driving directly the unitary fiducial marker device into the bone, the tubular protective guide collar includes a circumferential neck that has a slightly smaller inner diameter than an outer diameter of the substantially spherical imageable fiducial locator head; and holding the tubular protective guide collar in place against the patient to properly hold straight and orient the unitary fiducial marker device as the unitary fiducial marker device is driven directly into the bone;

wherein driving directly into the bone the unitary fiducial marker device includes moving the substantially spherical imageable fiducial locator head past the circumferential neck.

* * * * *